United States Patent [19]

Vinci et al.

[11] Patent Number: 5,744,350
[45] Date of Patent: Apr. 28, 1998

[54] DNA ENCODING TRIOL POLYKETIDE SYNTHASE

[75] Inventors: Victor A. Vinci, Charlottesville; Michael J. Conder, Harrisonburg, both of Va.; Phyllis C. McAda; Christopher D. Reeves, both of Woodenville, Wash.; John Rambosek, Seattle, Wash.; Charles Ray Davis, Lynnwood, Wash.; Lee E. Hendrickson, Carnation, Wash.

[73] Assignee: Merck & Co., Inc., Rahway, N.J.

[21] Appl. No.: 450,332

[22] Filed: May 25, 1995

Related U.S. Application Data

[63] Continuation of Ser. No. 148,132, Nov. 2, 1993, abandoned.
[51] Int. Cl.$^6$ .................... C12N 1/15; C12N 15/54
[52] U.S. Cl. ........... 435/254.11; 435/193; 435/252.3; 435/254.3; 435/254.5; 435/254.6; 435/320.1; 435/325; 536/23.2
[58] Field of Search ............... 435/254.11, 193, 435/254.3, 254.5, 254.6; 536/23.2, 23.74, 24.32

[56] References Cited

U.S. PATENT DOCUMENTS

| | | | |
|---|---|---|---|
| 4,231,938 | 11/1980 | Monaghan et al. | 549/292 |
| 4,346,227 | 8/1982 | Terahara | 560/119 |
| 5,151,365 | 9/1992 | Dombrowski et al. | 435/256.1 |
| 5,159,104 | 10/1992 | Dabora et al. | 560/119 |
| 5,182,298 | 1/1993 | Helms | 514/455 |
| 5,198,345 | 3/1993 | Gwynne et al. | 435/69.1 |
| 5,252,474 | 10/1993 | Gewain et al. | 435/172.3 |
| 5,362,638 | 11/1994 | Dahiya | 435/125 |

FOREIGN PATENT DOCUMENTS

0 556 699 A1  8/1993  European Pat. Off. .

OTHER PUBLICATIONS

Buckland, et al., "Production of lovastatin, an inhibitor of cholesterol accumulation in humans", Novel Microbial Products for Medicine and Agriculture, Ch. 19, pp. 161–169, 1989.

Hopwood, et al., "Molecular Products of Polyketides and its Comparison to Fatty Acids Biosynthesis", Annu. Rev. Genet., 1990, 24, pp. 37–66.

Moore, et al., "Biosynthesis of the Hypocholesterolemic Agent Mevinolin . . . ", J. Am. Chem. Soc., 1985, 107, pp. 3694–3701.

Endo, et al., "Dihydromonacolin L and Monacolin X, New Metabolites . . . ", The Journal of Antibiotics, vol. XXXVIII, No. 3, pp. 321–327, 1985.

Endo, et al., "Monacolin M, New Inhibitor of Cholesterol Biosynthesis", The Journal of Antibiotics, Dec. 1986, vol. XXXIX, pp. 1670–1673.

Springer, et al., "Terretonin, a Toxic Compound from *Aspergillus terreus*", J. Org. Chem., vol. 44, No. 26, pp. 4852–4854 (1979).

Arai, et al., "Pravastatin Sodium (CS–514) A Novel Cholesterol Lowering Agent . . . ", Sankyo Kenkyusho Vempo, 40, 1–38 (1988).

Drugs of the Future, vol. 12, No. 5, 1987 "Eptastatin Sodium".

Mayorga, et al., "The Developmentally Regulated Aspergillus . . . ", Mol. Gen. Genet., 235(2–3): 205–212 (Nov. 1992).

Leadley, et al., "The Erythromycin–Producing Polyketide Synthase", Biochem. Soc. Trans. 21 (1):218–222 (Feb. 1993).

Cortes, et al., "An Unusually Large Multifuctional Polypeptide . . . ", Nature, 348: 176–178 (Nov. 1990).

Bevitt, et al., "6–Deoxyerythromolide–B Synthase . . . ", Eur. J. Biochem., 204: 39–49 (Feb. 1992).

Beck, et al., "The Multifunctional 6–Methylsalicylic Acid Synthase Gene . . . ", Eur. J. Biochem., 192: 487–498 (Dept. 1990).

Hutchinson, et al., "The Genetic and Biochemical Basis of Polyketide Metabolism . . . ", Planta Med. 57(7) (Suppl. 1): 536–543 (Oct. 1991).

Primary Examiner—David L. Fitzgerald
Assistant Examiner—Brian K. Lathrop
Attorney, Agent, or Firm—Michael D. Yablonsky; Jack L. Tribble

[57] ABSTRACT

DNA encoding triol polyketide synthase (TPKS) has been isolated, purified and sequenced. Expression vectors comprising TPKS, cells transformed with the expression vectors, and processes employing the transformed cells are provided.

6 Claims, 30 Drawing Sheets

| | | | |
|---|---|---|---|
| CTGCAGTCAA | CGGATCACTT | ACCATTGCTG | TCGCCAAAAA | TATCCGTGAT | AATCCCGCTG | 60 |
| GCTTCATTGG | CAAGAGGCTT | GACGTACTTG | GGAGCTTGGG | TCTGGAACTG | GTTCATAACC | 120 |
| ACCTTGGTGA | TGAGATGTGC | ATCCCTCGTG | ACTTCCTTGA | ATCCATCGAA | TCCGGGAAGA | 180 |
| TGAGAGTGAA | AGTCCTGATG | AGAGCACGAA | GATCAGTAAG | TCAGGTCCTC | ACAGCGGAAG | 240 |
| CAGTTGCAAA | GAACGGTGGA | CTCCTTACCG | TGCCCAAGAA | CTTGTACATA | CAGAGCTCTT | 300 |
| TCATCTTGCG | AAACTCATCG | GCCATAGAGG | AGGGAAGAAT | GGTGCAGTAC | CCAGAGTCGA | 360 |
| CTATGAACCG | AATGGGCTTA | TCATTTGCG | AGAACCAGCT | CTCAATCCAT | GACGGTGCAT | 420 |
| TCGCATCAAA | ATCCCGTTTG | GCCCTCATGG | TCGTCAGTTC | CCACCATGTT | TTCGGATTGA | 480 |
| ACACCGGCAG | ATCAGATCTC | CGGCCACTCG | AGCACAGGTA | AAGAAGAAGG | CATAGTAGCC | 540 |
| CCGCACTGGT | AGTGACCAAG | GGGCAAAACC | ACGAGCCATG | TTGCTGCGTG | TCATTCCAAG | 600 |
| CCAGCGGACAG | AAGGTGGTGC | GGCTGTGTGA | GCGGGTCGAC | AGTCATGGCT | AGGAGACCAG | 660 |
| GTGTGGGTTGA | GGGATAAGAT | ATCGAGAGTG | ATGTGAGCAA | AAGATCCGGG | AAAGGTCGCG | 720 |

FIG. 1A

```
AAGGAAAGGG CGTCTCTCTT ACCAAGAAAG TCTGTTCCCT ATCATGCAAT CACCGCTTGC    780
TGTACGGTGG TGATGATGCT GGGATGGTGG TGGGTCCCCA CCGAATAACG CCGGACAGCT    840
GTTGAAGCCG AATGACGCCG GCAGGCCAAA AGAACCCTAC CTTCACTTAC TCAATCGGCG    900
CTTCCCCTCC TATCACCAAA TCGGATGTAA ATGGACGGGC CTTAATAGCG ACCGCCCGGG    960
CCGGGAATCC CCAAACGTAG ATAGATAGGC ATAGACCCGA AATCTTTGGC CCGGCATACA   1020
TGAGCACAGG AAGTTTCACG CGACGGGCGCC TTTCCTGCCT CAGCTTCAAT CCAAGCTCAC   1080
GAGTTCTGTC GCCTCTATCA GTCGTGCAAT TGTCCTACTG CAAACAGCAT GGCTCAATCT   1140
ATGTATCCTA ATGAGCCTAT TGTCGTGGTC GGCAGTGGTT GTCGCTTCCC TGGTGACGCC   1200
AACACACCCT CCAAGCTCTG GGAGCTACTC CAGCATCCTC GCGATGTGCA GAGTCGAATC   1260
CCCAAAGAAC GATTTGACGT CGACACATTT TATCACCCGG ACGGGAAGCA CCACGGGCGA   1320
ACAAATGCAC CCTACGCCTA TGTTCTCCAA GACGATCTGG GCGCCCTTCGA TGCGGCCTTC   1380
TTCAATATCC AGGCTGGAGA GGCCGAGAGT ATGGACCCCC AGCACCGGCT GTTGCTGGAG   1440
```

FIG. 1B

```
ACGGTGTACG AGGCCGTAAC GAATGCTGGA ATGCGTATCC AGGATCTGCA GGGAACTTCG   1500
ACTGCTGTTT ACGTCGGGGT GATGACGCAC GACTATGAGA CTGTCTCAAC CCGCGACCTG   1560
GAGAGCATCC CCACCTACTC GGCGACGGGT GTCGCGGTCA GTGTTGCGTC CAACCGCATC   1620
TCGTATTTT TTGACTGGCA TGGACCAAGT GTAAGTCACC CAATATCGTG TAGCAGTCTA    1680
ATCATGCCTCT AACGGACCGG GATGGTTGAA AGATGACGAT CGATACGGCA TGCAGCTCGT  1740
CGTTGGTTGC CGTTCATCTG GCGGTGCAAC AGCTACGGAC GGGTCAAAGC TCCATGGCAA   1800
TTGCTGCGGG TGCGAATCTG ATTCTGGGGC CCATGACATT CGTCCTTGAA AGCAAATTGA   1860
GCATGCTATC CCCCTCGGGT CGATCCCGCA TGTGGGACGC CGGAGCTGAC GGCTATGCCA   1920
GAGGCGTGAG TGTTCTTGA GCTCGTAGAT GACAGTTCCC ATCGCTGACC GTGATCAGGA    1980
AGCTGTTTGC TCTGTAGTGT TGAAGACATT GAGTCAAGCC TTGCGCGATG GGGACACGAT   2040
```

FIG. 1C

```
TGAATGTGTC ATCCGAGAAA CTGGGGTGAA TCAAGATGGC CGAACGACCG GAATTACGAT    2100
GCCGAACCAT AGTGCTCAGG AGGCACTCAT CAAGGCTACC TACGCCCAGG CTGGCCTTGA    2160
CATCACCAAG GCCGAGGACA GGTGCCAATT CTTCGAGGCT CATGGTCAGC AAAGAGAACC    2220
TGTTCTGTTG GCGCCCTGCA GCTGACATTC GTATGATAGG GACTGGTACT CCGGCCGGAG    2280
ATCCCCAGGA GGCGGAGGCC ATTGCAACAG CCTTCTTCGG CCACGAGCAG GTAGCACGCA    2340
GCGACGGAAA CGAGAGGGCC CCTCTGTTCG TGGGCAGTGC GAAAACTGTT GTCGGGCACA    2400
CCGAGGGCAC GGCCCGGTCTG GCTGGTCTCA TGAAGGCGTC GTTCGCTGTC CGCCATGGGG    2460
TAATCCCCCC CAACCTGCTG TTCGACAAAA TCAGCCCGCG AGTCGCCCCA TTCTATAAAA    2520
ACCTGAGGAT TCCGACAGAA GCTACCCAAT GGCCAGCTCT CCCACCCGGA CAACCGCGCC    2580
GCGCCAGTGT CAACTCCTTT GGTAAGCGAG GATTGCCCGG AGGAACCCTC ACAAGTACTC    2640
```

FIG.1D

```
GAATTAATGC TAACTGAACC GCGCCGATGG ACAGGATTCG GCGGCACGAA TGCGCATGCC  2700
ATTATTGAGG AATACATGGA GCCAGAGCAA AACCAGCTGC GAGTCTCGAA TAATGAGGAC  2760
TGCCCACCCA TGACCGGTGT CCTGAGTTTA CCCTTAGTCC TCTCGGGCGAA GTCCCAGCGC  2820
TCCTTAAAGA TAATGATGGA GGAGATGCTG CAATTCCTTC AGTCTCACCC CGAGATACAC  2880
TTGCACGACC TCACCTGGTC CTTACTGCGC AAGCGGGTCAG TTCTACCCTT CCGCCGGGCT  2940
ATTGTCGGCC ATAGTCATGA AACCATCCGC CGGGCTTTGG AGGATGCCAT CGAGGATGGT  3000
ATTGTGTCGA GCGACTTCAC TACGGAGGTC AGAGGCCAGC CATCGGTGTT GGGAATCTTC  3060
ACCGGGCAGG GGGCGCAGTG GCCGGGGGATG TTAAAGAATC TGATAGAGGC ATCGCCATAT  3120
```

FIG.1E

```
GTGCGGAACA TAGTGAGGGA GCTGGACGAC TCCCTGCAGA GCTTGCCGGA AAAATACCGG   3180
CCCTCGTGGA CGCTACTGGA CCAGTTCATG CTAGAAGGAG AGGCCTCCAA CGTCCAATAT   3240
GCTACTTTCT CCCAGCCATT ATGCTGCGCG GTGCAAATTG TCCTGGTCCG TCTCCTTGAA   3300
GCCGCGAGAA TACGATTCAC GGCTGTTGTT GGACATAGCT CCGGCGAAAT TGCTTGCGCC   3360
TTTGCTGCCG GGCTCATCAG TGCCTCGTTG GCGATTCGGA TTGCTTACTT ACGTGGAGTC   3420
GTCTCGGCAG GGGGCCCAG AGGCACACCG GGAGCCATGT TGGCCGCCGG GATGTCCTTT   3480
GAGGAAGCAC AAGAGATCTG CGAGTTGGAT GCCTTTGAGG GCCGCATCTG CGTGGCTGCC   3540
AGCAATTCCC CAGACAGTGT AACTTTCTCT GGCGACGCGA ACGCAATTGA TCACCTGAAG   3600
GGCATGTTGG AGGATGAGTC CACTTTTGCG AGACTGCTCA AGGTCGATAC AGGGTACCAC   3660
```

FIG.1F

```
TCGCATCATA TGCTTCCATG TGCAGACCCA TATATGCAAG CCCTAGAAGA GTGTGGTTGT    3720
GCTGTTGCCG ATGCAGGTTC CCCAGCCCGA AGTGTACCCT GGTATTCGTC CGTGGACGCC    3780
GAGAACAGGC AAATGGCAGC AAGAGACGTG ACCGCCAAGT ACTGGAAAGA TAACTTAGTA    3840
TCTCCCGGTGC TATTCTCCCA CGCAGTGCAG CGGGCAGTCG TCACGCACAA GGGGCTGGAT   3900
ATCGGGATTG AAGTGGGCTG TCACCCAGCT CTCAAGAGCC CATGCGTCGC CACCATCAAG    3960
GATGTCCTAT CTGGGGTTGA CCTGGGGTAT ACAGGTTGCT TGGAGCGAGG AAAGAATGAT    4020
CTCGATTCAT TCTCTCGAGC ACTGGCATAT CTCTGGGAAA GGTTTGGTGC CTCCAGTTTC    4080
GATGCGGACG AGTTCATGCG TGCAGTCGCG CCTGATCGGC CCTGTATGAG TGTGTCGAAG    4140
CTCCTACCGG CCTATCCATG GGACCGCTCT CGTCGCTACT GGGTGGAATC CCGAGCAACT    4200
```

FIG. 1G

```
CGCCACCATC TTCGAGGGCC CAAGCCCCAT CTTCTATTAG GAAAGCTCTC CGAATACAGC    4260
ACTCCGCTAA GCTTCCAGTG GCTGAATTTT GTGCGCCCAC GAGACATTGA ATGGCTTGAT    4320
GGACATGCAT TGCAAGGCCA GACTGTCTTC CCTGCGGGCCG GCTATATCGT CATGGCAATG    4380
GAAGCAGCCT TAATGATTGC TGGCACCCAC GCAAAGCAGG TCAAGTTACT GGAGATCTTG    4440
GATATGAGCA TTGACAAGGC GGTGATATTT GACGACGAAG ACAGCTTGGT TGAGCTCAAC    4500
CTGACAGCTG ACGTGTCTCG CAACGCCGGC GAAGCAGGTT CAATGACCAT AAGCTTCAAG    4560
ATCGATTCCT GTCTATCGAA GGAGGGTAAC CTATCCCTAT CAGCCAAGGG CCAACTGGCC    4620
CTAACGATAG AAGATGTCAA TCCCAGGACG ACTTCCGCTA GCGACCAGCA CCATCTTCCC    4680
CCGCCAGAAG AGGAACATCC TCATATGAAC CGTGTCAACA TCAATGCTTT CTACCACGAG    4740
CTGGGGTTGA TGGGGTACAA CTACAGTAAG GACTTCCGGC GTCTCCATAA CATGCAACGA    4800
```

FIG.1H

```
GCAGATCTTC GAGCCAGCGG CACCTTAGAC TTCATTCCTC TGATGGACGA GGGTAATGGC    4860
TGTCCCTCTCC TGCTGCATCC TGCATCATTG GACGTCGCCT TCCAGACTGT CATCGGGCA    4920
TACTCCTCCC CAGGTGATCG GCGTCTACGC TGTCTGTATG TACCCACTCA CGTTGATCGC    4980
ATCACACTTG TCCCATCCCT TTGCCTGGCA ACGGCTGAGT CCGGATGCGA GAAGGTTGCC    5040
TTCAATACTA TCAATACGTA CGACAAGGGA GACTACTTGA GCGGTGACAT TGTGGTGTTT    5100
GACGCGGAGC AGACCACCCT GTTCCAGGTT GAAAATATTA CTTTTAAGCC CTTTTCACCC    5160
CCGGATGCTT CAACTGACCA TGCGATGTTT GCCCGATGGA GCTGGGGTCC GTTGACTCCG    5220
GACTCGCTGC TGGATAACCC GGAGTATTGG GCCACCGGCG AGGACAAGGA GGCGATTCCT    5280
```

FIG. 1I

```
ATTATCGAAC GCATCGTCTA CTTCTATATC CGATCGTTCC TCAGTCAGCT TACGCTGGAG   5340
GAGGCCCAGC AGGCAGCCTT CCATTTGCAG AAGCAGATCG AGTGGCTCGA ACAAGTCCTG   5400
GCCAGGCGCCA AGGAGGGTCG TCACCTATGG TACGACCCCG GGTGGGAGAA TGATACTGAG   5460
GCCCAGATTG AGCACCTTTG TACTGCTAAC TCCTACCACC CTCATGTTCG CCTGGTTCAG   5520
CGAGTCGGCC AACACCTGCT CCCACCGTA CGATCGAACG GCAACCCATT CGACCTTCTG   5580
GACCACGATG GGCTCCTGAC GGAGTTCTAT ACCAACACAC TCAGCTTCGG ACCCGCACTA   5640
CACTACGCCC GGGAATTGGT GGGCCAGATC GCCCATCGCT ATCAGTCAAT GGATATTCTG   5700
GAGATTGGAG CAGGGACCGG CGGCGCTACC AAGTACGTGT TGGCCACGCC CCAGCTGGGG   5760
TTCAACAGCT ACACATACAC CGATATCTCC ACCGGATTCT TCGAGCAAGC GCGGGAGCAA   5820
TTTGCCCCCT TCGAGGACCG GATGGTGTTT GAACCCCTCG ATATCCGCCG CAGTCCCGCC   5880
```

FIG. 1J

```
GAGCAGGGCT TCGAGCCGCA TGCCTATGAT CTGATCATTG CCTCCAATGT GCTACATGCG    5940
ACACCCGACC TAGAGAAAAC CATGGCTCAC GCCCGCTCTC TGCTCAAGCC TGGAGCCAG    6000
ATGGTTATTC TGGAGATTAC CCACAAAGAA CACACACGGC TCGGGTTTAT CTTTGGTCTG    6060
TTCGCCGACT GGTGGGCTGG GGTGGATGAT GGTCGCTGCA CTGAGCCGTT TGTCTCGTTC    6120
GACCGCTGGG ATGCGGATCCT AAAGCGTGTC GGGTTTTCCG GTGTGGACAG TCGCACCACG    6180
GATCGGGACG CAAATCTATT CCCGACCTCT GTGTTTAGTA CCCATGCAAT TGACGCCACC    6240
GTGGAGTACT TAGACGCGCC GCTTGCCAGC AGCGGCACCG TCAAGGACTC TTACCCTCCC    6300
TTGGTGGTGG TAGGAGGGCA GACCCCCCAA TCTCAGCGTC TCCTGAACGA TATAAAAGCG    6360
ATCATGCCTC CTCGTCCGCT CCAGACATAC AAGCGCCTCG TGGATTTGCT AGACGCGGAG    6420
GAGCTGCCGA TGAAGTCCAC GTTTGTCATG CTCACGGAGC TGGACGAGGA ATTATTCGCC    6480
```

FIG. 1K

```
GGGCTCACTG AAGAGACCTT CGAGGCAACC AAGCTGCTGC TCACGTACGC CAGCAATACG    6540
GTCTGGCTGA CAGAAAATGC CTGGGTCCAA CATCCTCACC AGGCGAGCAC GATCGGCATG    6600
CTACGCTCCA TCCGCCGGGA GCATCCTGAC TTGGGAGTTC ATGTTCTGGA CGTCGACGCG    6660
GTTGAAACCT TCGATGCAAC CTTCCCTGGTT GAACAGGTGC TTCGGCTTGA GGAGCATACG   6720
GATGAGCTGG CCAGTTCAAC TACATGGACT CAAGAACCCG AGTCTCCTG GTGTAAAGGC     6780
CGCCCGTGGA TTCCTCGTCT GAAGCGCGAT CTGGCTCGCA ATAACCGAAT GAACTCCTCG    6840
CGCCGTCCCA TATACGAGAT GATCGATTCG TCGCGGGCTC CCGTGGCATT ACAGACGGCT    6900
CGGGATTCAT CATCCTACTT CTTGGAGTCC GCTGAAACCT GGTTTGTGCC TGAGAGTGTT    6960
CAGCAGATGG AAACAAAGAC GATCTATGTC CACTTTAGCT GTCCCCATGC GCTTAGGGTC    7020
```

FIG. 1L

```
GGACAGCTCG GGTTTTCTA  TCTTGTGCAG GGTCACGTCC AGGAGGGCAA TCGCGAAGTG  7080
CCGTCGTGG  CCTTAGCAGA GCGTAACGCA TCCATTGTGC ACGTTCGTCC CGATTATATA  7140
TATACTGAGG CAGATAACAA TCTGTCTGAG GGTGGTGGCA GCCTTATGGT AACCGTCCTC  7200
GCCGGCGGG  TGTTGGGCGA GACGGTGATC AGTACCGCCA AGTGCCTGGG GGTAACTGAC  7260
TCAATCCCTG TTCTGAATCC CCCCAGCATA TGTGGGCAGA TGTTGCTCCA TGCTGGTGAA  7320
GAGATCGGTC TTCAAGTTCA TCTGGCCACC ACTTCTGGCA GCTCGGACA  GGTTTCTGCT  7380
GGAGACGCCA AGTCCCTGGCT AACATTGCAT GCTCGCGACA CGGACTGGCA CCTGCGACGG  7440
GTACTGCCCC GGGGTGTCCA GGCTTTAGTC GACTTATCAG CCGACCAGAG CTGTGAAGGT  7500
TTGACTCAGA GGATGATGAA AGTTCTGATG CCTGGCTGTG CCCATTACCG TGCGGCAGAC  7560
```

FIG.1M

```
CTGTTCACAG  ACACCGTTTC  CACTGAATTG  CATAGCGGAT  CGCGGCATCA  AGCTTCACTG   7620
CCCGCCGCAT  ATTGGGAGCA  TGTGGTATCC  TTAGCCCGCC  AGGGACTTCC  TAGTGTCAGC   7680
GAGGGGTGGG  AGGTGATGCC  GTGCACTCAA  TTTGCAGCGC  ATGCCGACAA  GACGCGCCCG   7740
GATCTCTCGA  CAGTTATTTC  CTGGCCCCGG  GAGTCGGACG  AGGCTACGCT  TCCTACCAGG   7800
GTTCGCTCCA  TTGACGCTGA  GACCCTCTTT  GCGGCCGACA  AAACATATCT  CCTGGTCGGA   7860
CTGACTGGAG  ATCTTGGACG  ATCACTAGGT  CGTTGGATGG  TCCAGCCATGG  GGCCTGCCAC  7920
ATTGTACTTA  CGAGCAGAAA  TCCGCAGGTG  AACCCCAAGT  GGCTGGCGCA  TGTTGAAGAA   7980
CTGGGTGGTC  GAGTCACTGT  TCTTTCCATG  TAAGAGGAGT  CCTTCCTTCT  GCAATTCCTC   8040
CTTATGATCC  CGACTAACGC  AGCTGGCTTC  AGGGACGTGA  CAAGCCAAAA  CTCAGTGGAA   8100
GCTGGCCTGG  CTAAACTCAA  GGATCTGCAT  CTGCCACCAG  TGGGGGGTAT  TGCCTTTGGC   8160
```

FIG. 1N

```
CCTCTGGTTC TGCAGGATGT GATGCTAAAT AATATGGAAC TGCCAATGAT GGAGATGGTG    8220
CTCAACCCCA AGGTCGAAGG CGTCCGCATC CTGCACGAGA AGTTCTCCGA TCCGACCAGT    8280
AGCAACCCTC TCGACTTCTT CGTGATGTTC TCCTCGATTG TGGCCGTCAT GGGCAACCCG    8340
GGTCAGGCTA ACTACAGTGC GGCTAACTGC TACCTTCAAG CGCTGGGCA GCAGCGAGTT    8400
GCATCCGGAT TAGCAGTACG TTTTCACTCC ATCCTTTGCT AAACACTCCT ATGGGCCTTT    8460
ACTAAACCGG GCAGGCGTCC ACCATCGACA TCGGTGCCGT GTACGGCGTT GGGTTCGTCA    8520
CTCGGGGGGA GCTGGAGGAG GACTTTAATG CAATTCGGTT CATGTTCGAT TCGGTTGAGG    8580
AACATGAACT GCATACACTG TTTGCTGAGG CAGTGGTGGC CGGTCGACGA GCCGTGCACC    8640
AGCAAGAGCA GCAGCGGAAG TTCGGCGACAG TGCTCGACAT GGCTGATCTG GAACTGACAA    8700
```

FIG. 10

```
CCGGAATTCC GCCCCTGGAT CCAGCCCTCA AAGATCGGAT CACCTTCTTC GACGACCCCC  8760
GCATAGGCAA CTTAAAAATT CCGGAGTACC GAGGGGCCAA AGCAGGCCAA GGGGCAGCCG  8820
GCTCCAAGGG CTCGGTCAAA GAACAGCTCT TGCAGGCGAC GAACCTGGAC CAGGTCCGTC  8880
AGATCGTCAT CGGTAAGTTG AGCGAATCCG GGGAATATTC TCCCCTTCCT CACTCAGCGG  8940
ACTGGAGATT AACCGCTTCT TTTCCTTTGG CAGATGGACT CTCCGCGAAG CTGCAGGTGA  9000
CCCTGCAGAG CCCCGATGGG GAAAGCGTGC ATCCCACCAT CCTGGTTCTC CCCACTAATC  9060
TGGACTCTCT GGGGCGGGTC ACCGTGGGAA CCTGGTGCTT CGATCACCGA CAAGCAGCTG  9120
TGCCACTCCT GAAAGTGCTT GGGGGTGCTT GGGGGTGCTG TCTCGCTAAT TACCTTGATT  9180
CGGCGATTGCC ACCTAGCTCC ATTCCCCTCG TCGCAGCCAC CGACGGGGGT GAGGCTGCTG  9240
CTGACAATAC TTCCGAGAAT GAAGTTTCGG GACGCGAGGA TACTGACCTT AGTGCCGCCG  9300
```

FIG. 1P

```
CCACCATCAC TGAGCCCTCG TCTGCCGACG AAGACGATAC GGAGCCCGGGC GACGAGGACG   9360
TCCCGGGTTC CCACCATCCA CTGTCTCTCG GGCAAGAATA CTCCTGGAGA ATCCAGCAGG   9420
GAGCCGAAGA CCCCACCGTC TTTAACAACA CCATTGGTAT GTTCATGAAG GGCTCTATTG   9480
ACCTTAAACG GCTGTACAAG GCGTTGAGAG CGGTCTTGCG CCGCCACGAG ATCTTCCGCA   9540
CGGGGTTTGC CAACGTGGAT GAGAACGGGA TGGCCCAGCT GGTGTTTGGT CAAACCAAAA   9600
ACAAAGTCCA GACCATCCAA GTGTCTGACC GAGCCGGGGC CGAAGAGGGC TACCGACAAC   9660
TGGTGCAGAC ACGGTATAAC CCTGCCGCAG GAGACACCTT GGGGCTGGTG GACTTCTCT   9720
GGGGCCAGGA CGACCATCTG CTGGTTGTGG CTTACCACCG ACTCGTCGGG GATGGATCTA   9780
CTACAGAGAA CATCTTCGTC GAAGCGGGCC AGCTCTACGA CGGCACGTCG CTAAGTCCAC   9840
```

FIG. 1Q

```
ATGTCCCTCA GTTTGCGGAC CTGGCGGCAC GGCAACGCGC AATGCTCGAG GATGGGAGAA    9900
TGGAGGAGGA TCTCGCGTAC TGGAAGAAAA TGCATTACCG ACCGTCCTCA ATTCCAGTGC    9960
TCCCACTGAT GCGGCCCCTG GTAGGTAACA GTAGCAGGTC CGATACTCCA AATTCCAGC   10020
ACTGTGGACC CTGGCAGCAG CACGAAGCCG TGGCGCGACT TGATCCGGATG GTGGCCTTCC  10080
GCATCAAGGA GCGCAGTCGC CTCACCGACA AGCACAAGG CGACGCCGAT GCAGTTCTAT CTGGCGGCGT  10140
ATCAGGTGCT GTTGGCGCGC AAGCACAAGG CCATGGGGTT CACCGTGGGC CTCGCCGACA  10200
CCAACCGTGC GACTGTCGAC GAGATGGCGG CCATGGGGTT CTTCGCCAAC CTCCTTCCCC  10260
TGCGCTTCCG GGATTTCCGC CCCCATATAA CGTTTGGCGA GCACCTTATC GCCACCCGTG  10320
ACCTGGTGCG TGAGGCCTTG CAGCACGCCC GCGTGCCCTA CGGCGTCCTC CTCGATCAAC  10380
```

FIG. 1R

```
TGGGGCTGGA GGTCCCCGGTC CCGACCAGCA ATCAACCTGC GCCTTTGTTC CAGGCCGTCT    10440

TCGATTACAA GCAGGGCCAG GCGGAAAGTG GAACGATTGG GGGTGCCAAG ATAACCGAGG    10500

TGATTGCCAC GCGCGAGCGC ACCCCTTACG ATGTCGTGCT GGAGATGTCG GATGATCCCA    10560

CCAAGGATCC GCTGCTCACG GCCAAGTTAC AGAGTTCCCG CTACGAGGCT CACCACCCTC    10620

AAGCCTTCTT GGAGAGCTAC ATGTCCCTTC TCTCTATGTT CTCGATGAAT CCCGCCCTGA    10680

AGCTGGCATG ATGGCGCAAA CATAGAACAT GATAGGCGCAG CAGGGACGAT GTAGATAGAG    10740

CTTTGCTTCT GCGGGTGGAT CTATAATATA GTATATATAA ATATGGTGAG CCGAACGAAG    10800

AGGGGGGAAT GCCACAATTA TTTACTGTTT TGCGCCCGTAC ACGAGGAGAA GACGTCCAGA    10860

ACAACATAAA TATATCACTC TAGTGAGACA CCATATATTC GGAGAGACTA TAAAAATATA    10920

CATCTACTCC AATGTCTGGG CCGTCACACA CAGCTTACGA AAACGATTAA TGACCTCCAA    10980
```

FIG.1S

```
CACGTCGCGC  GGTCGATTGG  GAAACTGATG  CTGCCCAGCA  AACTCCAATA  CCTGCGCCTC   11040
TCGGGGGAG   AAATGGCGCG  CCACCAGCAT  CTTCGATCCT  GCGAGCGCAA  AATCATCGCG   11100
ACCTGCAGA   TGTAATGTCG  GTATCCGAAT  GACCAGTTCC  TCCTGCCACT  CGGTATCTTT   11160
GCTGTCGTTG  TCGTCGTCAT  GGTTCTTCAT  CATTCGTTCC  TCATATACTG  GCTTGCCTCG   11220
TCTTGATACC  AGGGACAGAT  CAACAGGCGCA CACTCATCC   GGGGCAACCA  GGGCAGGTGA   11280
CCCATCTGCT  GCTGCCAGAG  GTCACCAGGG  GTCACCAGGG  CACCTTCGGA  GAAACCGATA   11340
GCACCCACGA  TAGGGATGTG  GGGGTGTTGA  GTCTGCCAGT  CGACAATGGT  GCGGCGGATG   11400
GGGTCGTGGA  CGGCGGCGAG  GCGTTCGCTC  ACGGAGGGTC  CATTATGATT  GTTGTCGCTG   11460
CTGCTTTCAA  ACCAGGAGTA  ATATGGCCCT  AGGTCGGGCGA AGACGGGGAG  AATCCCAGGC   11520
CCTGCAGAGG  AAGGGAACGG  AGCTGTCACG  TAGACGAATT  C                        11561
```

FIG. 1T

```
            10          20          30          40          50
      1234567890  1234567890  1234567890  1234567890  1234567890
      MAQSMYPNEP  IVVVGSGCRF  PGDANTPSKL  WELLQHPRDV  QSRIPKERFD    50

VDTFYHPDGK  HHGRTNAPYA  YVLQDDLGAF  DAAFFNIQAG  EAESMDPQHR    100

LLLETVYEAV  TNAGMRIQDL  QGTSTAVYVG  VMIHDYETVS  TRDLESIPTY    150

SATGVAVSVA  SNRISYFFDW  HGPSMTTDTA  CSSSLVAVHL  AVQQLRTGQS    200

SMAIAAGANL  ILGPMTFVLE  SKLSMLSPSG  RSRMWDAGAD  GYARGEAVCS    250

VVLKTLSQAL  RDGDTTECVI  RETGVNQDGR  TIGTTMPKHS  AQEALIKATY    300

AQAGLDITKA  EDRCQFFEAH  GTGTPAGDPQ  EAEAIATAFF  GHEQVAPGGG    350

NERAPLFVGS  AKTVVGHTEG  TAGLAGLMKA  SFAVRHGVIP  PNLLFIKISP    400

RVAPFYKNLR  IPTEATQWPA  LPPGQPRRAS  VNSFGFGGIN  AHAIIEEYME    450

PEQNQLRVSN  NEDCPPMTGV  LSLPLVLSAK  SQRSLKIMME  EMLQFLQSHP    500

EIHLHDETWS  LLRKRSVLPF  RRAIVGHSHE  TEAAALEDAI  EDGIVSSDIT    550

TEVRGQPSVL  GIFTGQGAQW  PGMLKNLIEA  SPVYRNIVRE  LDDSLQSLPE    600

KYRPSWTLLD  QFMLEGEASN  VQYATFSQPL  CCAVQIVLVR  LLEAARIRFT    650

AVVGHSSGEI  ACAFAAGLIS  ASLAIRIAYL  RGVVSAGGAR  GTPGAMLAAG    700

MSFEEAQEIC  ELDAFEGRIC  VAASNSPDSV  TFSGDANAID  HLKGMLEDES    750

TFARLLKVDT  AYHSHHMLPC  ADPYMQALEE  CGCAVADAGS  PAGSVPWYSS    800

VDAENRQMAA  RDVTAKYWKD  NLVSPVLFSH  AVQRAVVIHK  ALDIGIEVGC    850

HPALKSPCVA  TIKDVLSGVD  LAYTGCLERG  KNDLDSFSRA  LAYLWERFGA    900

SSFDADEFMR  AVAPDRPQMS  VSKLLPAYPW  DRSRRYWVES  RATRHHLPGP    950
```

FIG.2A

```
          10         20         30         40         50
    1234567890 1234567890 1234567890 1234567890 1234567890
    KPHLLLGKLS EYSTPLSFQW LNFVRPRDIE WLDGHALQGQ TVFPAAGYTV  1000

MAMEAALMIA GTHAKQVKLL ETLDMSIDKA VIFDDEDSLV ELNLTADVSR  1050

NAGEAGSMTI SFKIDSCLSK EGNLSLSAKG QLALTIEDVN PRTTSASDQH  1100

HLPPPEEEHP HMNRVNINAF YHELGLMGYN YSKDFRRLHN MQRADLRASG  1150

TLDFIPLMDE GNGCPLLLHP ASLDVAFQTV IGAYSSPGDR RLRCLYVPTH  1200

VDRITLVPSL CLATAESGCE KVAFNTTNTY DKGDYLSGDI VVFDAEQTTL  1250

FQVENTTFKP FSPPDASTDH AMFARWSWGP LTPDSLLDNP EYWATAQDKE  1300

AIPIIERIVY FYIRSFLSQL TLEERQQAAF HLQKQIEWLE QVLASAKEGR  1350

HLWYDPGWEN DTEAQIEHLC TANSYHPHVR LVQRVGQHLL PTVRSNGNPF  1400

DLLDHDGLLT EFYTNTLSFG PALHYARELV AQIAHRYQSM DILEIGAGTG  1450

GATKYVLATP QLGFNSYTYT DISTGFFEQA REQFAPFEDR MVFEPLDIRR  1500

SPAEQGFEPH AYDLIIASWV LHATPDLEKT MAHARSLLKP GGQMVILETT  1550

HKEHTRLGFI FGLFADWWAG VDDGRCTEPF VSFDRWDAIL KRVGFSGVDS  1600

RTIDRDANLF PTSVFSTHAI DATVEYLDAP LASSGTVKDS YPPLVVVGGQ  1650

TPQSQRLLND IKAIMPPRPL QTYKRLVDLL DAEELPMKST FVMLTELDEE  1700

LFAGLTEETF EATKLLLTYA SNTVWLTENA WVQHPHQAST IGMLRSIRRE  1750

HPDLGVHVLD VDAVETFDAT FLVEQVLRLE EHTDELASST TWTQEPEVSW  1800

CKGRPWIPRL MRDLARNNRM NSSRRPIYEM IDSSRAPVAL QTARDSSSYF  1850

LESAETWFVP ESVQQMETKT IYVHFSCPHA LRVGQLGFFY LVQGHVQEGN  1900

REVPVVALAE RNASIVHVRP DYTYTEADNN LSEGGGSLMV TVLAAAVLAE  1950
```

FIG.2B

```
           10         20         30         40         50
  1234567890 1234567890 1234567890 1234567890 1234567890
TVISTAMCLG VIDSILVLNP PSICGQMLLH AGEEIGLQVH LATTSGNRSS   2000

VSAGDAKSAL TLHARDTDWH LRRVLPRGVQ ALVDLSADQS CEGLTQRMMK   2050

VIMPGCAHYR AADLFTDTVS TELHSGSRHQ ASLPAAYWEH VVSLARQGLP   2100

SVSEGWEVMP CTQFAAHADK TRPDLSTVIS WPRESDEATL PTRVRSIDAE   2150

TLFAADKTYL LVGLTGDLGR SLGRWWVQHG ACHIVLTSRN PQVNPKWLAH   2200

VEELGGRVTV LSMDVTSQNS VEAGLAKLKD LHLPPVGGIA FGPLVLQQVM   2250

LNNMELPMME MVLNPKVEGV RILHEKFSDP TSSNPLDFFV MFSSIVAVMG   2300

NPGQANYSAA NCYLQALAQQ RVASGLAAST IDIGAVYGVG FVTRAELEED   2350

FNAIRFMFDS VEEHELHTLF AEAVVAGRRA VHQQEQQRKF ATVLDMADLE   2400

LTTGIPPLDP ALKDRITFFD DPRIGNLKIP EYRGAKAGEG AAGSKGSVKE   2450

QLLQATNLDQ VRQIVIDGLS AKLQVTLQIP DGESVHPTIP LIDQGVDSLG   2500

AVTVGTWFSK QLYLDLPLLK VLGGASITDL ANEAAARLPP SSIPLVAATD   2550

GGAESTDNTS ENEVSGREDT DLSAAATTTE PSSADEDDTE PGDEDVPRSH   2600

HPLSLGQEYS WRIQQGAEDP TVFNNTIGMF MKGSIDLKRL YKALRAVLRR   2650

HEIFRTGFAN VDENGMAQLV FGQTKNKVQT IQVSDRAGAE EGYRQLVQTR   2700

YNPAAGDTLR LVDFFWGQDD HLLVVAYHRL VGDGSTTENI FVEAGQLYDG   2750

TSLSPHVPQF ADLAARQRAM LEDGRMEEDL AYWKKMHYRP SSIPVLPLMR   2800

PLVGNSSRSD TRNFQHCGPW QQHEAVARLD RMVAFRIKER SRKHKATPMQ   2850

FYLAAYQVLL ARLTDSTDLT VGLADINRAT VDEMAAMGFF ANLLPLRFRD   2900

FRPHITFGEH LIATRDLVRE ALQHARVPYG VLLDQLGLEV PVPTSNQPAP   2950

LFQAVFDYKQ GQAESGTIGG AKITEVIATR ERTPYDVVLE MSDDPTKDPL   3000

LTAKLQSSRY EAHHPQAFLE SYMSLLSMFS MNPALKLA              3038
```

FIG.2C

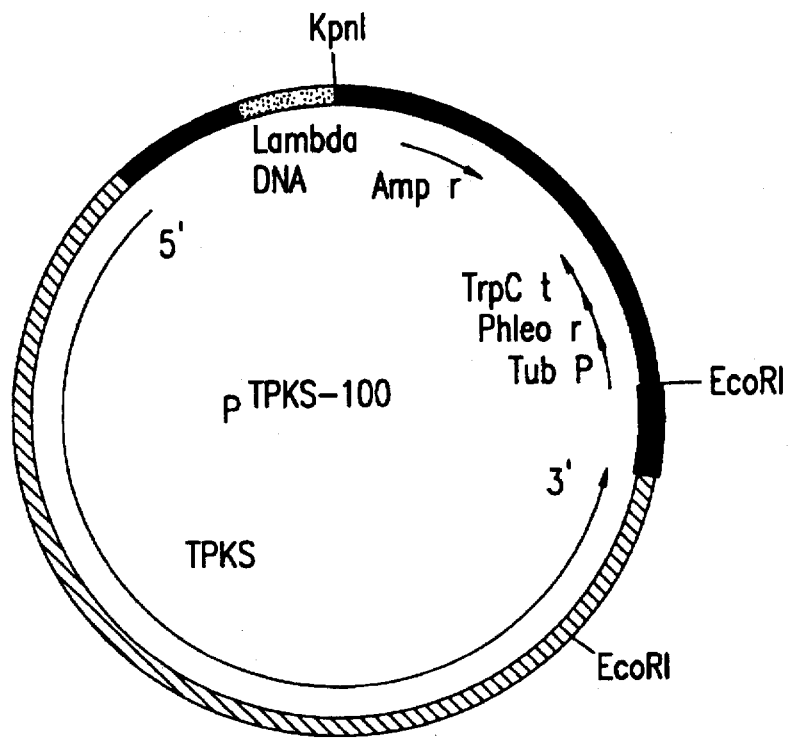
ASPERGILLUS TERREUS DNA:
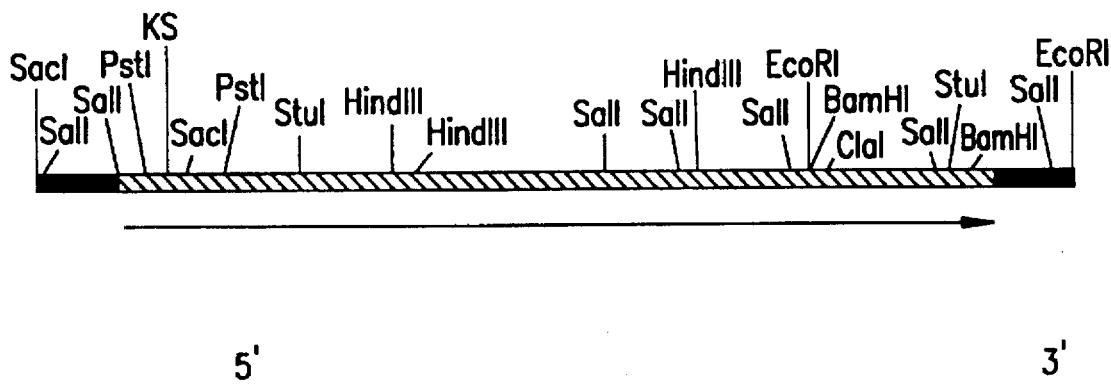
FIG.3

KETO ACYLSYNTHASE ALIGNMENT

```
FAS_RATF   (130-229)    YSMVGCQRAM MANRLSFFFD FKGPSIALDT ACSSSLLALQ NAYQAIRSGE
TRIOL PKS  (150-249)    YSATGVAVSV ASNRISYFFD WHGPSMTIDT ACSSSLVAVH LAVQQLRTGQ
MSAS_PENPA (173-272)    WMGIGTAYCG VPNRISYHLN LMGPSTAVDA ACASSLVAIH HGVQAIRLGE

Consensus               ...G...... ..NR.S.... ..GPS...D. AC.SSL.A.. ...Q.R.G.
```

ACETYL/MALONYL TRANSFERASE ALIGNMENT

```
MSAS_PENPA (621-671)    SDRVQILTYV MQIGLSALLQ SNGITPQAVI GHSVGEIAAS VVAGALSPAE
FAS_RATF   (553-603)    F--V-SL-TA IQIALIDLLT SMGLKPDGII GHSLGEVACG YADGCLSQRE
TRIOL PKS  (626-676)    F--SQPLCCA VQIVLVRLLE AARIRFTAVV GHSSGEIACA FAAGLISASL

Consensus               .......... ..L...QI.L.LL. .......... GHS.GE.A.. ...G..S...
```

DEHYDRATASE ALIGNMENT

```
MSAS_PENPA (943-982)    YTTRLDNDTK PFPGSHPLHC TEIVPAAGLI NTFLKGTGGQ
FAS_RATF   (863-902)    NIDASSESSD HYLVDHCIDG RVLFPCTGYL YLVWK-TLAR S
TRIOL PKS  (970-1010)   WLNFVRPRDI EWLDGHALQG QTVFPAAGYI VMAMEAALMI A

Consensus               .......... ......H..G .....P..G. .........
```

FIG.5

ENOYL REDUCTASE ALIGNMENT

```
TRIOL PKS  (1903-1950)   VPVVALAERN ASIVHVRPDY IYTEADNNLS EGGGSLMVTV LAAAVLAE
FAS_RATF   (1642-1691)   VPVVYTAYY  SLVVRGRIQH GETVLIHSGS GGVGQAAISI ALSLGCRVFT
SU4 ER                   VPIAYTTAHY ALHDLAGLRA GQSVLIHAAA GGVGMAAVAL ARRAG-LAEV

Consensus                VP........ .......... .......... .G.G...... ..........
```

KETO REDUCTASE ALIGNMENT

```
TRIOL PKS  (2141-2196)   PTRVRSIDAE TLFAADKTYL LVGLTGDLGR SLGRWMVQHC ACHIVLTSRN
MSAS_PENPA (1398-1451)   LP-ASEG-PR LLPRPEGTYL ITGGLGVLGL EVADFLVEKG ARRLLLISRR
FAS_RATF   (1864-1921)   PTLISAI-SK TFCPEHKSYI ITGGLGGFGL ELARWLVLRG AQRLVLTSRS

Consensus                .......... .......... .Y..G.G.G. .......... V.G.A....L.SR.
```

ACYL CARRIER PROTEIN ALIGNMENT

```
TRIOL PKS  (2461-2548)   VRQIVIDGLS AKLQVTLQIP DGESVHPTIP LIDQGVDSLG AVTVGTWFSK
FAS_RATF   (2114-2201)   GDGEAQRDLV KAVAHILGIR DLAGINLDSS LADLGLDSLM GVEVRQILER
MSAS_PENPA (1697-1758)   -KAYLDEKIR GCVAKVLQMT A-EDVDSKAA LADLGVDSVM TVTLRRQLQ-

Consensus                .......... .......... .L........ L.D.G.DS.. V.........
```

| Potential SAM Binding Region in Methyl Transferase | |
|---|---|
| Consensus | △△△D/E△GXGXGX△XXX△△△⋀/P |
| TPKS (1444) | I L E I GAGTGG A TKY V L P |

△ = hydrophobic A.A.
X = any A.A.
⋀ = charged A.A.

FIG. 8 ized to scaling up the process,
improving the culture medium or, simplifying the isolation
train. The present invention focuses on a method of increasing process yield wherein the increase in productivity is due
to the use of a microorganism that produces increased levels
of HMG-CoA reductase inhibitor.

It may be desirable to increase the biosynthesis of HMG-
CoA reductase inhibitors at the level of gene expression.

5,744,350

1
DNA ENCODING TRIOL POLYKETIDE SYNTHASE

This is a continuation, of application Ser. No. 08/148,
132, filed Nov. 2, 1993, now abandoned.

BACKGROUND OF THE INVENTION

Hyperchloesterolemia is known to be one of the prime
risk factors for ischemic cardiovascular diseases such as
arteriosclerosis. Cholesterol and other lipids are transported
in body fluids by lipoproteins of varying density. The two
lipoproteins carrying the majority of cholesterol in the blood
are low-density lipoproteins (LDL) and high-density lipoproteins (HDL). The role of LDL is to transport cholesterol
to peripheral cells outside the liver. LDL-receptors on a cell
plasma membrane bind LDL and allow entry of cholesterol
into the cell. HDL may scavenge cholesterol in the tissues
for transport to the liver and eventual catabolism. LDL levels
are positively correlated with the risk of coronary artery
disease while HDL levels am negatively related, and the
ratio of LDL-cholesterol to HDL-cholesterol has been
reported to be the best predictor of coronary artery disease.
Thus substances which effectuate mechanisms for lowering
LDL-cholesterol may serve as effective antihypercholesterolemic agents.

Mevacor® (lovastatin; mevinolin) and ZOCOR®
(simvastatin), now commercially available, are two of a
group of very active antihypercholesterolemic agents that
function by inhibiting the enzyme HMG-CoA reductase.
Lovastatin and related compounds inhibit cholesterol synthesis by inhibiting the rate-limiting step in cellular cholesterol biosynthesis, namely the conversion of hydroxymethylglutarylcoenzyme A (HMG-CoA) into mevalonate by
HMG-CoA reductase [3.7–9.12]. HMG-CoA reductase
inhibitors act through cellular homeostatic mechanisms to
increase LDL receptors with a consequent reduction in
LDL-cholesterol and a resultant therapeutic antihypercholesterolemic effect. The HMG-CoA reductase inhibitors
within this invention include, but are not limited to compactin (ML-236B), lovastatin, simvastatin, pravastatin, fluvastatin and mevastatin.

Many HMG-CoA reductase inhibitors am synthesized by
microorganisms. The general biosynthetic pathway of the
HMG-CoA reductase inhibitors of the present invention has
been outlined by Moore et al., who showed that the biosynthesis of mevinolin (lovastatin) by *Aspergillus terreus* ATCC
20542 proceeds from acetate via a polyketide pathway (R.
N. Moore et al., Biosynthesis of the hypocholesterolemic
agent mevinolin by *Aspergillus terreus*. Determination of
the origin of carbon, hydrogen, and oxygen atoms by $^{13}C$
NMR and mass spectrometry. J. Amer. Chem. Soc., 1985,
107: 3694–3701). Endo and his coworkers demonstrated
that similar biosynthetic pathways existed in *Pencillium
citrinum* NRRL 8082 and *Monascus ruber* M-4681 (A. Y.
Endo et al., Biosynthesis of ML-236B (compactin) and
monacolin K., 1985, J. Antibiot. 38: 444–448).

The recent commercial introduction of HMG-CoA reductase inhibitors has provided a need for high yielding processes for their production. Methods of improving process
yield include, but are not limited to scaling up the process,
improving the culture medium or, simplifying the isolation
train. The present invention focuses on a method of increasing process yield wherein the increase in productivity is due
to the use of a microorganism that produces increased levels
of HMG-CoA reductase inhibitor.

It may be desirable to increase the biosynthesis of HMG-
CoA reductase inhibitors at the level of gene expression.

2

Such increases could be achieved by increasing the concentration in an HMG-CoA reductase inhibitor-producing
microorganism of one or more of the enzymes or enzymatic
activities in the biosynthetic pathway of the HMG-CoA
reductase inhibitor. It may be particularly desirable to
increase the concentration of a rate-limiting biosynthetic
activity.

Triol polyketide synthase (TPKS) is a multifunctional
protein with at least four activities as evidenced by the
product of the enzymatic activity (Moore, supra). TPKS is
believed to be the rate-limiting enzymatic activity(ies) in the
biosynthesis of the HMG-CoA reductase inhibitor compounds.

The present invention identifies a DNA encoding triol
polyketide synthase (TPKS) from *Aspergillus terreus*. The
DNA encoding the TPKS of the present invention has been
isolated, purified and sequenced. Complementary DNA
(cDNA) and genomic DNA sequences corresponding to
TPKS have been prepared. The TPKS cDNA of the present
invention may be used to increase the production of HMG-
CoA reductase inhibitors by HMG-CoA reductase inhibitor-
producing microorganisms The TPKS cDNA of the present
invention may also be used to produce purified TPKS.

SUMMARY OF THE INVENTION

DNA encoding the full-length form of triol polyketide
synthase (TPKS) is identified. The DNA is sequenced and
cloned into expression vectors. Cells transformed with the
expression vectors produce increased levels of TPKS and
increased levels of HMG-CoA reductase inhibitors. The
DNA is useful to produce recombinant full-length TPKS.
The DNA may be used to isolate and identify homologues of
TPKS present in organisms that are capable of producing
polyketides, particularly microorganisms that are capable of
producing HMG-CoA reductase inhibitors.

BRIEF DESCRIPTION OF THE DRAWINGS

FIGS. 1A–1T is the nucleotide sequence of triol
polyketide synthase.

FIGS. 2A–2C is the predicted amino acid sequence of
triol polyketide synthase.

FIG. 3 shows pTPKS100.

FIG. 5 shows the alignments of keto acyl synthase,
acetyl/malonyl transferase and dehydratase carried out on
regions of TPKS, rat fatty acid synthase (FAS) and *P.
patulum* 6MSAS (SEQ ID NO:4, SEQ ID NO:5, SEQ ID
NO:6, SEQ ID NO:7, SEQ ID NO:8, SEQ ID NO:9, SEQ ID
NO:10, SEQ ID NO:11, SEQ ID NO:12, SEQ ID NO:13,
SEQ ID NO:14, SEQ ID NO:15).

FIG. 6 shows the alignments of enoyl reductase, keto
reductase and acyl carrier protein carried out on regions of
TPKS (SEQ ID NO:16, SEQ ID NO:17, SEQ ID NO:18,
SEQ ID NO:19, SEQ ID NO:20, SEQ ID NO:21, SEQ ID
NO:22, SEQ ID NO:23, SEQ ID NO:24, SEQ ID NO:25,
SEQ ID NO:26, SEQ ID NO:27).

Figure 7:
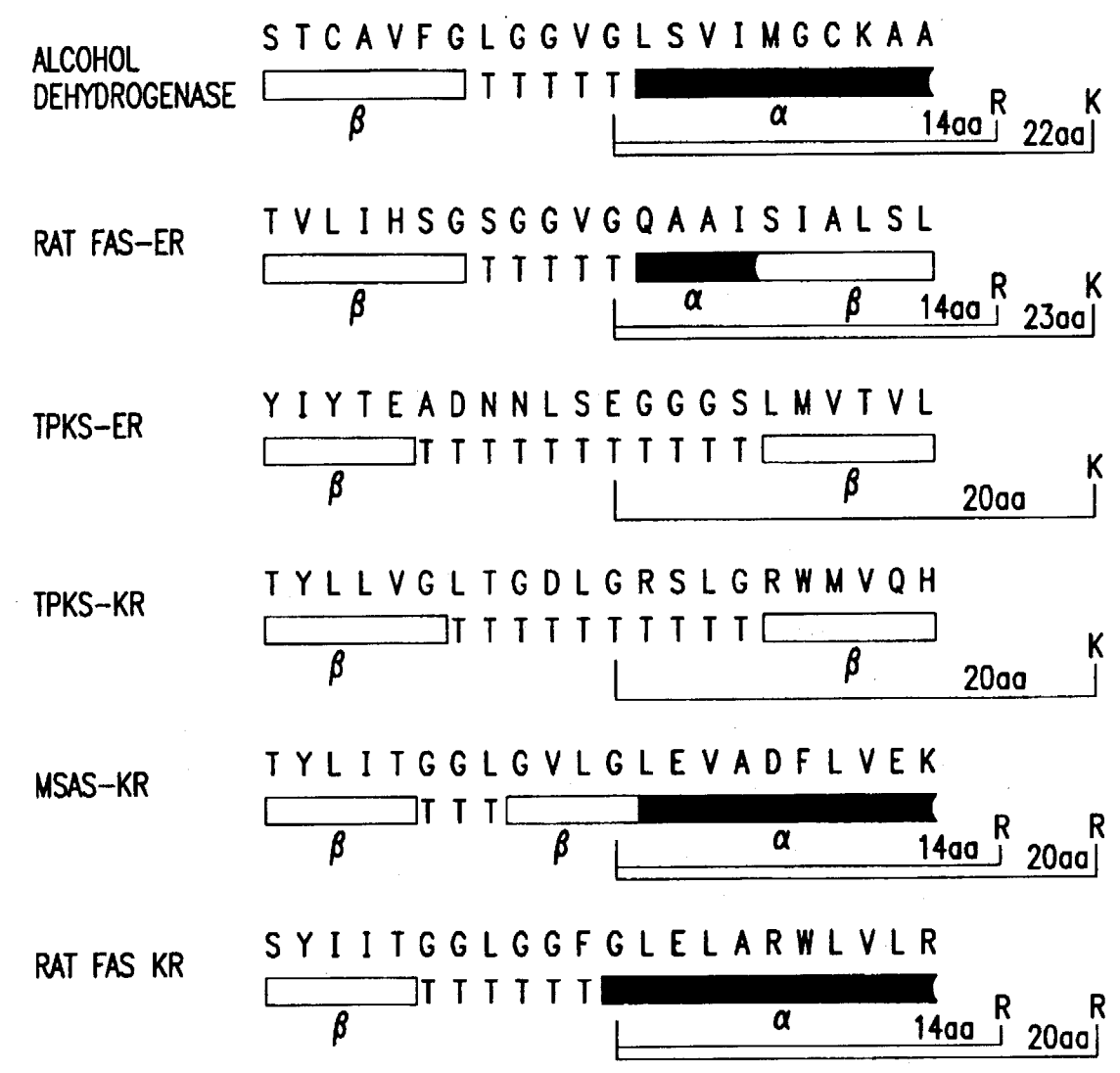

FIG. 7 is a Chou-Fasman secondary structure prediction
of pyridine nucleotide binding regions of TPKS and related
proteins (SEQ ID NO:28, SEQ ID NO:29, SEQ ID NO:30,
SEQ ID NO:31, SEQ ID NO:32, SEQ ID NO:33).

FIG. 8 shows the S-adenosylmethionine binding regions
of a variety of prokaryotic and eukaryotic methyl transferases (SEQ ID NO:34).

DETAILED DESCRIPTION OF THE INVENTION

Figure 4:
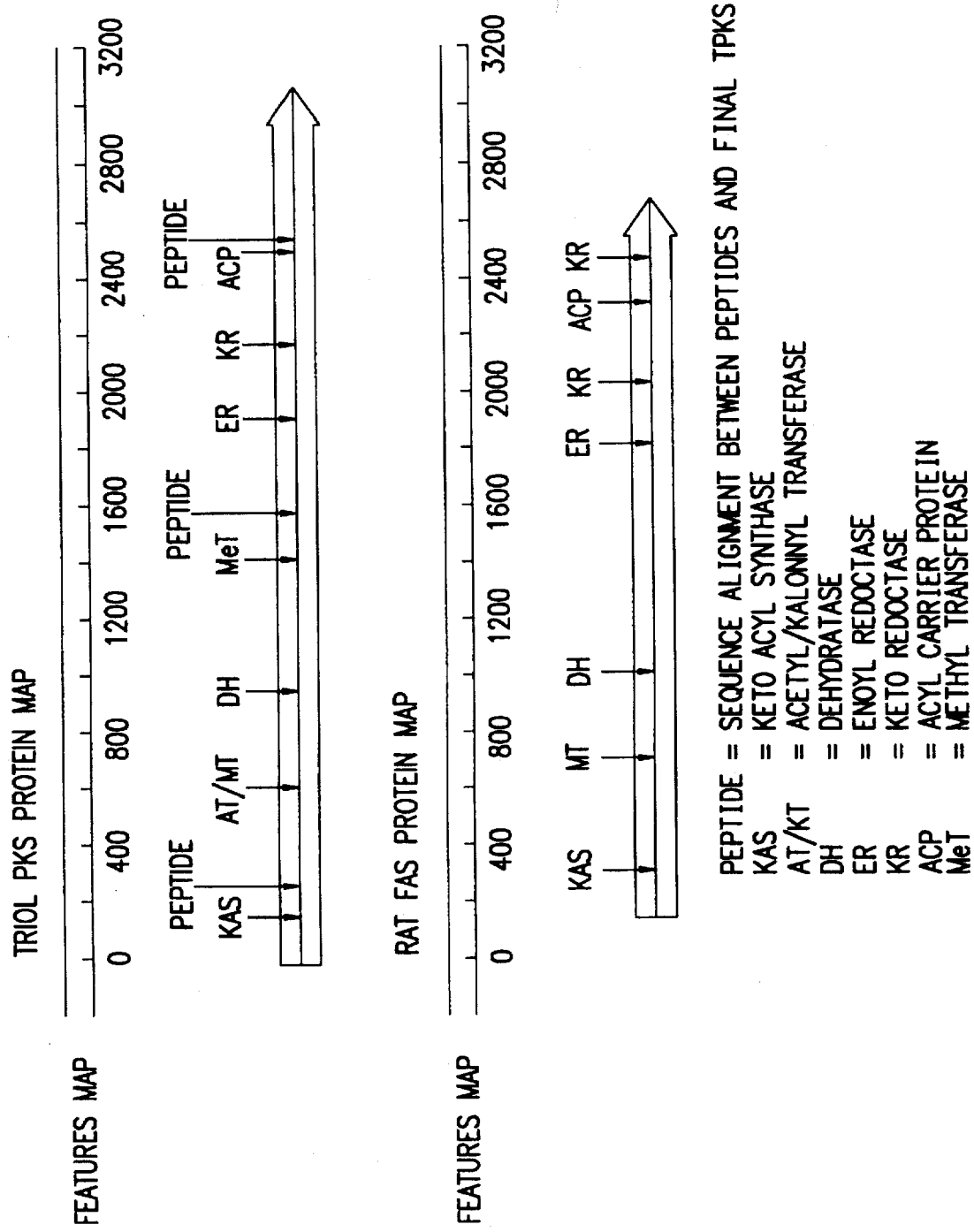
FIG. 4 is a graphic view of the open reading frame of the
TPKS protein and the overall placement of the TPKS
peptides and PKS activities established by alignments generated by the Intelligenetics GeneWorks program.
Figure 9:
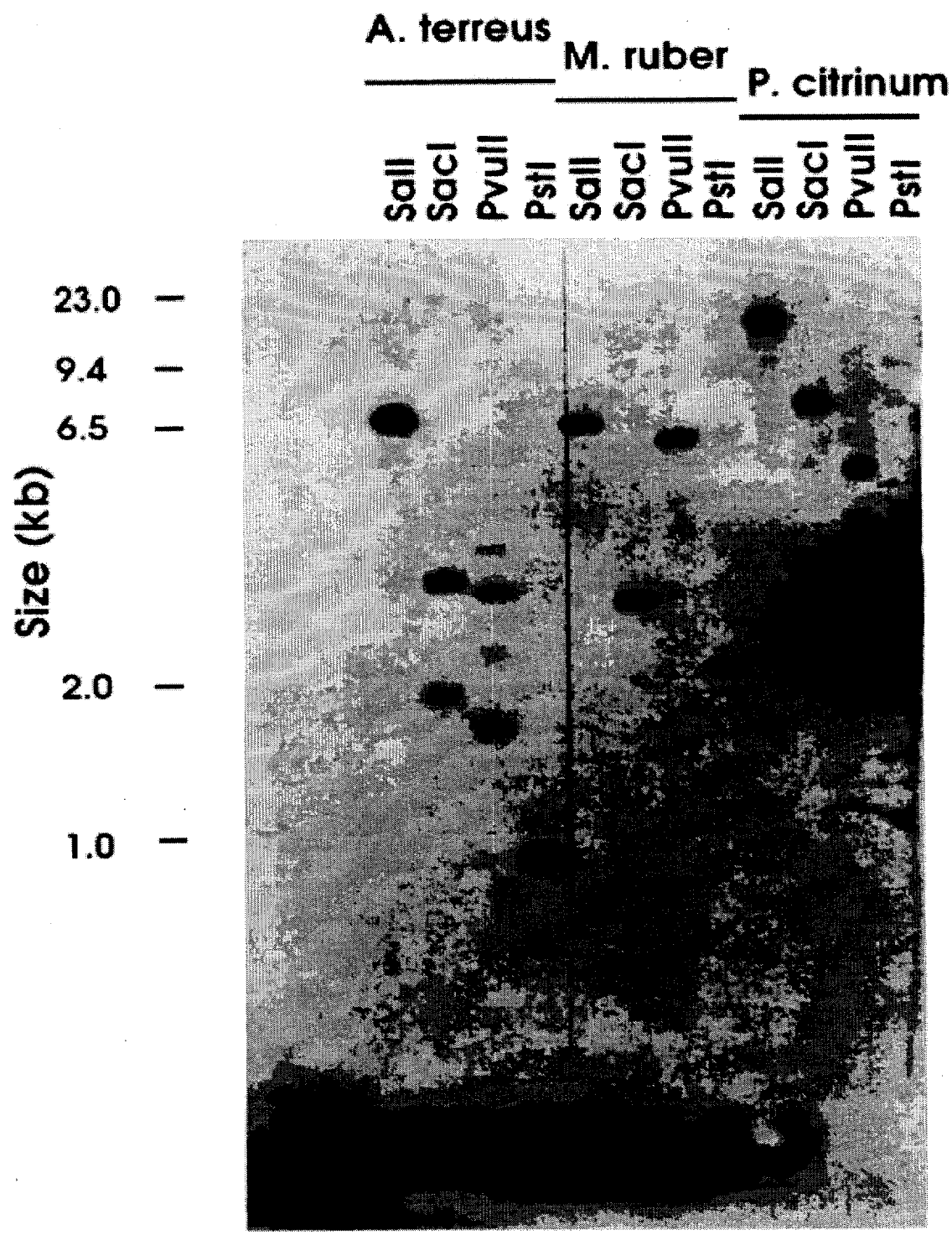
FIG. 9 is a Southern blot showing the homology of ketoacylsynthase of the TPKS of *A. terreus* to *M. ruber* and *P. citrinum*.

The present invention relates to a DNA molecule encoding triol polyketide synthase (TPKS) which is isolated from TPKS-producing cells. Cells capable of producing TPKS include, but are not limited to, strains of *Aspergillus terreus*, *Monascus ruber*, *Penicillum citrinum*, *Penicillum brevicompactum*, *Hypomyces chrysospermus*, *Paecilomyces sp* M2016, *Eupenicillium sp.* MM603, *Trichoderma longibrachiatum* M6735 and *Trichoderma pseudokoningii* M6828.

TPKS, as used heroin, refers to enzymatic activities that convert acetate precursors and S-adenosyl methionine to an intermediate in the triol biosynthetic pathway. This intermediate is further modified to produce a triol nonaketide. Polyketide synthases from bacteria and fungi employ common enzymatic functions to synthesize polyketides from two carbon units (for a review, see D. A. Hopwood and D. H. Sherman, 1990, Comparison to fatty acid biosynthesis, Ann. Rev. Genet. 24: 37–66).

Polyketides am an important class of natural products because of their structural diversity and because many have antibiotic or other pharmaceutical activities. Most of the economically important polyketides are produced by fungi or actinomycetes.

Polyketide biosynthesis is similar to that of fatty acid biosynthesis in that it involves the sequential condensation of carboxylate units. Unlike fatty acids, which are built from acetate units, polyketides may be built from acetate, propionate, or butyrate units. Additionally, some or all of the β-keto groups added at each cycle of condensation during polyketide biosynthesis are left unreduced, or are reduced only to hydroxyl or enoyl functionalities. This variation in building units and the variation in modification of the beta-keto groups results in a tremendous variety of products as well as difficulty in comparing biosynthetic genes from different pathways.

*Aspergillus terreus* is a filamentous soil fungus; different strains of *A. terreus* produce a variety of polyketides (Springer, J. et al., 1979, terretonin, a toxic compound from *Aspergillus terreus*, J. Org. Chem., Vol. 44, No. 26, 4852–4854). Lovastatin is a polyketide produced by certain strains of *A. terreus* (Moore, supra). In addition to lovastatin and related metabolites such as triol or monacolin J, other polyketides found in *A.terreus* include sulochrin and related structures (Curtis, R. G. et al., 1964, The biosynthesis of phenols, J. Biochem., 90: 43–51) derived from emodin (Fujii, L, et al., 1982, Partial purification and some properties of emodin-o-methyltransferase from (+)-geodin producing strain of *Aspergillus terreus*. Chem. Pharm. Bull. 30(6) :2283–2286); terreic acid (Sheehan, J. C. et al., 1958, J. Am. Chem. Soc. 80: 5536); patulin (D. M. Wilson, 1976, Adv. Chem. Ser. No. 149) and citrinin (Sankawa, U. et al., 1983, Biosynthesis of citrinin in *Aspergillus terreus*, Tetrahedron, 39(21):3583–3591 ). Presumably each of these products is made by a specific PKS encoded by a specific and distinct PKS gene(s), thus increasing the difficulty in cloning the triol PKS.

The structure and activity of lovastatin was reported by A. Alberts et al. (Proc. Natl. Acad. Sci. U.S.A., 1980, 77: 3957–3961). Lovastatin is a reduced molecule consisting of a methylbutyryl group joined by an ester linkage to a nonaketide having a conjugated decene ring system.

Moore et al. (supra) described lovastatin biosynthesis. Proton and $^{13}C$ NMR studies of in vivo labeled lovastatin showed that all the carbons are derived from acetate except in the methyl groups at positions 6 and 2', which were derived from methionine. The triol molecule is composed of nine acetate units. The side-chain is composed of two acetate units. Esterification of triol and the butyrate side chain occurs enzymatically (Kimura, supra). The methyl butyrate side chain is presumably synthesized by a separate PKS. Lovastatin is first synthesized as a highly reduced precursor longer than 9 acetate units which undergoes reoxidation, including oxidative cleavage of a carbon-carbon bond.

Limited information is available for compactin biosynthesis. The most likely pathway would be nearly identical to that of lovastatin biosynthesis in *M. ruber* and *A. terreus*, except that methylation does not occur at the 6 position on the diene ring system.

Polyketide synthases (PKS) and fatty acid synthases (FAS) are classified by functional types. Type II enzymes, typical of bacteria and plants, have a separate polypeptide for each enzymatic activity. Type I enzymes, found in animals, bacteria and fungi, consist of large polypeptides with multiple activites or functional domains. Regions of amino acid sequence similarity have been identified in these genes: domains for ketoacyl synthase, acetyl/malonyl transferase, β-keto reductase, enoyl reductase, dehydratase and acyl carrier protein. The identification of these domains is considered evidence of the resulting enzymatic activity in light of the difficulty in obtaining functional Type I PKS in vitro (Sherman, supra).

Any of a variety of procedures may be used to molecularly clone the TPKS genomic DNA or complementary DNA (cDNA). Thes methods include but are not limited to, direct functional expression of the TPKS gene in an appropriate host following the construction of a TPKS-containing genomic DNA or cDNA library in an appropriate expression vector system. The preferred method consists of screening a TPKS-containing cDNA expression library constructed in a bacteriophage or vector with an antibody directed against the purified TPKS protein. The antibody is obtained by standard methods (Deutscher, M. (ed), 1990, Methods in Enzymology, Vol. 182) by isolating purified TPKS protein from HMG-CoA reductase inhibitor-producing cells, inoculating an appropriate host, such as a rabbit, with the purified protein and, after several boosts, collecting immune sera. Antibody collected from the animal is used to screen the cDNA expression library and cDNA clones expressing TPKS epitopes recognized by the antisera are selected. The positive clones am further purified, labeled and used to probe TPKS-containing genomic or cDNA libraries to identify related TPKS containing DNA. Standard restriction analysis of the related clones can be used to create a restriction map of the region and sequence analysis of the genomic and cDNA clones can be used to define a structural map and the open reading frame of the gene, respectively.

Another method of cloning TPKS involves screening a TPKS-containing cDNA library constructed in a bacteriophage or plasmid shuttle vector with a labelled oligonucleotide probe designed from the amino acid sequence of TPKS. The method may consist of screening an TPKS-containing cDNA library constructed in a bacteriophage or plasmid shuttle vector with a partial cDNA encoding the TPKS subunits. This partial cDNA is obtained by the specific PCR amplification of TPKS DNA fragments through the design of degenerate oligonucleotide primers from the amino acid sequence of the purified TPKS subunits.

It is readily apparent to those skilled in the art that other types of libraries, as well as libraries constructed from other cells or cell types, may be useful for isolating TPKS-encoding DNA. Other types of libraries include, but are not limited to, cDNA libraries derived from other cells or cell lines and genomic DNA libraries.

It is readily apparent to those skilled in the art that suitable cDNA libraries may be prepared from cells or cell lines which have TPKS activity. The selection of cells or cell lines for use in preparing a cDNA library to isolate TPKS cDNA may be done by first measuring cell associated TPKS activity using incorporation of radiolabelled acetate and separation of products by high performance liquid chromatography (HPLC).

Preparation of cDNA libraries can be performed by standard techniques well known in the art. Well-known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the an that DNA encoding TPKS may also be isolated from a suitable genomic DNA library. Construction of genomic DNA libraries can be performed by standard techniques well-known in the art. Well-known genomic DNA library construction techiques can be found in Maniatis et al. (supra).

In order to clone the TPKS gene, knowledge of the amino acid sequence of TPKS may be necessary. To accomplish this, TPKS protein may be purified and partial amino acid sequence determined by conventional methods. Determination of the complete amino acid sequence is not necessary. Once suitable amino acid sequences have been identified, the DNA sequences capable of encoding them are synthesized.

Because the genetic code is degenerate, more than one codon may be used to encode a particular amino acid, and therefore, the amino acid sequence can be encoded by any of a set of similar DNA oligonucleotides. Only one member of the set will be identical to the TPKS sequence but will be capable of hybridizing to TPKS DNA even in the presence of DNA oligonucleotides with mismatches. The mismatched DNA oligonucleotides may still hybridize to the TPKS DNA to permit identification and isolation of TPKS encoding DNA.

It is readily apparent to those skilled in the art that DNA encoding TPKS from a particular organism may be used to isolate and purify homologues of TPKS from other organisms. To accomplish this, the first TPKS DNA may be mixed with a sample containing DNA encoding homologues of TPKS under appropriate hybridization conditions. The hybridized DNA complex may be isolated and the DNA encoding the homologous DNA may be purified therefrom.

cDNA clones encoding TPKS may be isolated in a two-stage approach employing polymerase chain reaction (PCR) based technology and cDNA library screening.

Amino acid sequence information may be obtained by automated amino acid sequencing using Edman chemistry of both the intact protein and the peptide fragments generated by specific proteolytic cleavage. Following incubation for the prescribed periods, digestion is terminated and resulting peptide fragments are fractionated and detected.

TPKS in substantially pure form derived from natural sources according to the purification processes described herein, is found to be encoded by a single mRNA.

The cloned TPKS cDNA obtained through the methods described above may be expressed by cloning it into an expression vector containing a suitable promoter and other appropriate transcription regulatory elements, and transferred into prokaryotic or eukaryotic host cells to produce recombinant TPKS. Techniques for such manipulations am well-known in the art.

In order to simplify the following Examples and the Detailed Description, certain terms will be defined.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters.

An expression vector is a replicable DNA construct in which a DNA sequence encoding a TPKS is operably linked to suitable control sequences capable of effecting the expression TPKS in a suitable host. Control sequences include a transcriptional promoter, an optional operator sequence to control transcription and sequences which control the termination of transcription and translation.

Certain vectors, such as amplification vectors, do not need expression control domains but rather need the ability to replicate in a host, usually conferred by an origin of replication, and a selection gene to facilitate recognition of transformants.

A promoter is defined as a DNA sequence that directs RNA polymerase to bind to DNA and initiate RNA synthesis. A strong promoter is one which causes mRNAs to be initiated at high frequency.

DNA encoding TPKS may also be cloned into an expression vector for expression in a host cell. Host cells may be prokaryotic or eukaryotic, including but not limited to bacteria, yeast, mammalian and insect cells and cell lines.

The expression vector may be introduced into host cells via any one of a number of techniques including but not limited to transformation, transfection, protoplast fusion, and electroporation. The expression vector-containing cells are clonally propagated and individually analyzed to determine whether they contain the TPKS gene or produce TPKS protein. Identification of TPKS expressing host cell clones may be done by several means, including but not limited to immunological reactivity with anti-TPKS antibodies, and the presence of host cell-associated TPKS activity.

Expression of TPKS DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with micro-injection into frog oocytes being preferred.

PCR is the polymerase chain reaction, which is a technique for copying the complementary strands of a target DNA molecule simultaneously for a series of cycles until the desired amount is obtained.

Plasmids are generally designated by a low case p preceded or followed by capital letters and/or numbers. The starting plasmids used in this invention are commercially available, are publicly available on an unrestricted basis, or can be constructed from such available plasmids by conventional procedures. In addition other equivalent plasmids or constructs will be readily apparent to one skilled in the art.

Transformed host cells are cells which have been transformed or transfected with TPKS vectors constructed using recombinant DNA techniques. Expressed TPKS may be deposited in the cell membrane of the host cell or may be intracellular or may be secreted.

It is also well known, that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is also well known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate. Alteration of the amino acid sequence may lead to altered properties that in turn result in the production of modified structures; for example, the elimination of one of the reductase activities may result in the biosynthesis of a less-reduced compound.

The full-length TPKS-encoding DNA in plasmid pLOA was designated pTPKS100. A sample of pTPKS-100 in *E. coli* strain JM109, was deposited under the terms of the Budapest Treaty, on Sep. 15, 1993 in the permanent culture collection of the American Type Culture Collection, at 12301 Parklawn Drive, Rockville, Md., 20852, and has been assigned the Accession number ATCC 69416.

The following examples illustrate the present invention without, however, limiting the same thereto.

EXAMPLE 1

Culture Conditions

Three strains of *Aspergillus terreus* were used. The two lovastatin-producing strains included *A. terreus* ATCC 20542. A lovastatin nonproducing strain was also used. A lovastatin-nonproducing strain or a lovastatin-overproducing strain of *A. terreus* may be derived from lovastatin-producing strains of *A. terreus* that are publicly available; an example of a publicly-available strain is *A. terreus* MF-4833, which is deposited with the American Type Culture Collection under Accession No. 20542. One skilled in the art would appreciate that a variety of techniques such as mutagenesis techniques, including but not limited to ultraviolet irradiation, treatment with ethyl-methanesulfonate (EMS), exposure to nitrous acid, nitrosoguanidine and psoralen-crosslinking, could be used to generate a strain that does not produce or which overproduces lovastatin. The extent of the mutagenesis may be determined in a variety of ways including auxotrophy, i.e., the requirement of the mutated strain for a specific growth substance beyond the minimum required for normal metabolism and reproduction of the parent strain as well as measurement of production of lovastatin by individual cultures. An alternative monitoring system involves the use of an intercalating dye such as acriflavine, which prevents any growth of the parent (lovastatin-producing) strain when plated at 10,000 spores per plate but, following mutagenesis, allows growth of about 3–5 colonies per plate. Alternatively, the extent of mutagenesis may be monitored by visual observation of colonies having morphologies or colors that differ from the unmutagenized parent strain. Mutant strains are reisolated and pooled and subjected to further mutagenesis so that, by repetition of these procedures, mutated strains of *A. terreus* that do not produce or which overproduce lovastatin may be obtained.

*Monascus ruber* ATCC 20657 and *Penicillium citrinum* ATCC 20606 were used in hybridization studies.

The strains were maintained on YME+TE medium. The recipe for YME+TE medium is as follows:

0.4% Yeast Extract (w/v);
1.0% Malt Extract (w/v);
0.4% Glucose (w/v);
0.5% Trace Element (TE; v/v); and
2.0% agar (w/v) in 1 liter of water, pH 7.2.

The recipe for Trace Elements (TE) is as follows:

0.1% $FeSO_4$-$7H_2O$ (w/v);
0.1% $MnSO_4$-$H_2O$ (w/v);
0.0025% $CuCl_2.2H_2O$ (w/v);
0.0132% $CaCl_2.2H_2O$ (w/v);
0.0056% $H_3BO_3$ (w/v);
0.0019% $(NH_4)_6Mo_7O_{24}.4H_2O$ (w/v); and
0.02% $ZnSO_4.7H_2O$ (w/v) in 1 liter of water.

EXAMPLE 2

Fermentation Conditions

For the generation of spore stocks, single colonies were generated by growing on YME+TE plates for 8 days at 28° C. and 65% relative humidity. Single colonies were removed, and streaked on YME+TE slants. The slants were incubated for 8 days at 28° C. in 65% humidity. Spores were harvested by addition of 2 ml of Spore Suspension Solution (SSS). SSS contains 10% Glycerol (v/v) and 5% Lactose (w/v) in water. Spores were scraped into the SSS with a sterile inoculation loop and counted. The suspension was stored at −20° C.

A two-stage fermentation from spore suspensions was used for the production of lovastatin. A seed culture was started by inoculating $1 \times 10^8$ spores into 2 ml/15 ml culture tube of HLC medium.

The recipe for HLC medium is as follows:

1.5% $KH_2PO_4$ (w/v);
2.0% Cerelose (w/v);
0.1% Ardamine pH (Champlain Industries) (w/v);
1.5% Pharmamedia (Traders Protein) (w/v);
0.2% Lactic acid (v/v); and
0.4% ammonium citrate (w/v) in 1 liter of water.

The pH of HLC medium was adjusted to pH 7.2 before sterilization.

Cultures were shaken at a 30 degree angle at 28° C. for approximately 28 hours on a rotary shaker with a 70 mm diameter amplitude at 220 rpm. Two ml of seed culture was used to inoculate 25 ml of GP-9 medium in a 250 ml flask.

The recipe for GP-9 medium is as follows:

0.9% Ammonium Citrate (w/v);
0.12% Ardamine pH (w/v);

1.2% Cerelose (w/v);

4.0% Pharmamedia (w/v);

24.5% Lactose (w/v); and 0.2% P 2000 (v/v) in water at pH 7.2.

Incubation was continued as described for seed cultures without the 30 degree angle. Lovastatin production was monitored after days of fermentation.

A one stage fermentation of *A. terreus* cultures in CM media was used to generate vegetative mycelia for transformations or DNA preparations. Fermentations were started by inoculating $1 \times 10^8$ conidiospores into 50 ml of CM medium in a 250 ml flask and incubated as described.

The recipe for Complete Medium (CM) is as follows:

50 ml of Clutterbuck's salts;

2.0 ml Vogel's Trace elements;

0.5% Tryptone (w/v);

0.5% Yeast extract (w/v); and 1.0% Glucose (w/v) in one liter of water.

The recipe for Clutterbuck's salts is as follows:

12.0% $Na_2NO_3$ (w/v);

1.02% KCl (w/v);

1.04% $MgSO_4.7H_2O$ (w/v); and 3.04% $KH_2PO_4$ (w/v).

The recipe for Vogel's trace elements is as follows:

0.004% $ZnCl_2$ (w/v);

0.02% $FeCl_3$ (w/v);

0.001% $CuCl_2$ (w/v);

0.001% $MnCl_2.4H_2O$;

0.001% $NaB_4O_7.10H_2O$ (w/v); and 0.001% $(NH_4)_6MO_7O_{24}.7H_2O$ (w/v).

EXAMPLE 3

Construction of Vector, pLO9 pLO9 is a 5.6 kb vector constructed with features useful for both cosmid library construction and fungal transformations. For dominant selection in *Aspergillus terreus*, pLO9 contains a *Streptoalloteichus hindustanus* phleomycin resistance gene driven by an *A. niger* β-tubulin promoter and terminated by a *Saccharomyces cerevisiae* terminator sequence. For selection in *Escherichia coli*, the vector contains the ampicillin resistance gene and for lambda packaging, the vector contains a lambda cos site. The construction of pLO9 is described below.

The phleomycin resistance marker originated from *S. hindustanus* and the termination sequence is from the CYC1 gene in *S. cerevisiae*. Both sequences were isolated on one DNA fragment from pUT713 (CAYLA, Toulouse Cedex, France) by digesting pUT713 with the restriction enzymes BamH1 and BglII. The isolated fragment was cloned into BamH1-digested pUC18 to produce vector pLO1. The genomic copy of the β-tubulin gene from *A. niger* ATCC 1015, was cloned as a 4.3 kb EcoR1 fragment in pUC8 to create p35-C-14. Several modifications were made to the genomic sequence. An EcoRI site was introduced at the initiator ATG by in vitro mutagenesis. The HindIII site in the promoter was removed by digestion with exonuclease, filling in with Klenow, and religation. Finally, an upstream EcoRI site was changed to a PstI site by digestion with EcoRI, filling in with Klenow and addition of a PstI linker by religation with ligase. The β-tubulin promoter was then subcloned as a PstI to EcoRI fragment in pUC8 to create pC15-1. An XbaI site was introduced at the initiator ATG by digestion with EcoRI, filling in with Klenow, addition of a XbaI linker and religation. The resulting vector was named pTL-113.

The β-tubulin promoter was cloned upstream of the phleomycin gene by cutting pTL113 with PstI and XbaI and cloning the isolated promoter fragment into the PstI and XbaI sites of pLO1 to produce pLO3. The BglII site was removed with a fill in reaction followed by blunt-end ligation to produce vector pCS12. The PstI to Hind III fragment containing the beta tubulin promoter, phleomycin resistance gene, and the terminator sequence were cloned into a PUC8 vector to generate pLO6. The XbaI site at the ATG was removed by a fill-in reaction and ligation to give pLO7. The PstI to HindIII was moved as a fragment into a pUC18 backbone in which the XmaI site had been filled and replaced with a BglII linker. The resulting vector was named pLO8. A PstI fragment containing the lambda cos site from pJL21 was inserted into the vector to generate pLO9.

EXAMPLE 4

Isolation of Genomic DNA

Vegetative mycelia were generated in CM media for 48 hr at 220 rpm at 28° C. Mycelia were collected by filtration through cheesecloth and frozen in liquid nitrogen for lyophilization overnight. Lyophilized mycelia were ground with sand using a mortar and pestle and suspended in 5 ml of Breaking Buffer (100 mM NaCl; 50 mM EDTA; 10 mM Tris, pH 8.0; 1% SDS; 50 ug/ml pancreatic RNase; 50 ug/ml Proteinase K). The mix was transferred to a 125 ml flask and an equal volume of Tris-saturated phenol/chloroform (50:50) was added. The flask was shaken for 1 hour at 37° C. and 200 rpm. The aqueous layer was removed after centrifugation at 10,000 rpm for 10 minutes. The aqueous layer was extracted twice more with phenol/chloroform and was then extracted once with chloroform. DNA was precipitated from the aqueous layer by addition of 0.1 volume 3M NaCl and 2.5 volumes of ethanol and then freezing at −70° C. for 10 minutes. The precipitated DNA was collected by centrifugation at 10,000 rpm for 15 minutes. The pelleted DNA was dried and resuspended in a solution of 10 mM Tris-HCl, 1 mM EDTA, pH 7.5. DNA concentrations were determined by measuring absorbance at wavelength 260 nM.

EXAMPLE 5

Construction of *A. terreus* Libraries

A. Preparation of Genomic Fragments

*A. terreus* genomic DNA was isolated as described. Large random DNA fragments for insertion into the vectors were isolated by partially digesting 10 μg of DNA with the restriction enzyme Sau3A. The digested DNA was electrophoresed on a 1.0% Agarose gel. For the genomic library, an area containing 9–23 kb sized fragments was cut from the gel. For the cosmid library, another segment of the gel containing 30–60 kb sized fragments was excised. The large chromosomal DNA fragments contained in the gel slices were isolated by electroelution. The DNA was concentrated by addition of 0.1 volumes of 3M sodium acetate and 2.5 volumes of ethanol, freezing at −70° C. for 15 minutes, and centrifugation at 10,000 rpm for 10 minutes to precipitate the DNA.

B. Construction of the *A. terreus* Cosmid Library

The pLO9 cosmid DNA was used to supply the two arms and cos sites required for lambda packaging. Two fragments were isolated from pLO9 for the packaging reaction.

Fragment one was isolated by digesting pLO9 with XbaI, phosphatasing with HK phosphatase (Epicenter Technologies), digesting with BglII, electroeluting on a 1% Agarose gel, concentrating by the addition of 0.1 volumes of 3M sodium acetate and 2.5 volumes of ethanol, freezing at −70° C. for 15 minutes and centrifuging at 10,000 rpm for 10 minutes to precipitate the DNA.

Fragment two was isolated by digesting pLO9 with SmaI, phosphatasing with HK phosphatase and then digesting with BgIII. Fragment two was isolated with the procedure described for fragment one. Fragment one, fragment two and isolated *A. terreus* insert DNA were ligated in a 1:1:2 ratio at a concentration of 0.5 µg of each DNA.

C. Packaging into Lambda Phage and Plating

Packaging into lambda phage was accomplished by mixing the ligation mixture with 10 µl of extract A from *E. coli* strain BHB2688 (Amersham) and 15 µl of extract B from *E. coli* strain BHB2690 (Amersham). The packaging mix was incubated at 22° C. for 120 minutes. A volume of 500 µl of SM (0.58% NaCl(w/v); 0.20% $MgSO_4$(w/v); 0.05M Tris pH 7.5; 0.01% Gelatin(w/v)) and 10 µl of chloroform was then added to the packaging mix.

*E. coli* strain DH5 was prepared for transfection by growing cells to an optical density of 1.0 at wavelength 600 nm in LB+maltose medium. LB+maltose medium consists of 1.0% Bacto-tryptone (w/v); 0.5% Bacto-yeast extract (w/v); 1.0% NaCl (w/v); pH 7.5; 0.2% Maltose (v/v) is added after autoclaving.

The cells were centrifuged at 4,000 rpm for 10 minutes and resuspended in 10 mM $MgSO_4$. Fifty microliters of the packaging mix was added to 200 µl of the resuspended DH5 cells and incubated for 30 minutes at 37° C. A 500 µl of aliquot of LB medium was added and the mix was incubated for 30 minutes at 37° C. The cell mix was spread on LB agar plates containing 100 µg/ml ampicillin (Sigma) and incubated at 37° C. A total of 10,000 colonies were generated with this library.

D. Construction of the *A. terreus* Genomic Library

The lambda replacement vector, EMBL3 (Promega), was used for the construction of the genomic library. The vector was purchased as predigested arms ready for ligation with the genomic inserts. The two arms were ligated to the 9–23 kb genomic inserts at a ratio of 1:1:2, packaged into lambda phage, and plated for hybridization with selected probes as described above.

EXAMPLE 6

A. Isolation of Cosmid DNA from *E. coli*

The *A. terreus* cosmid library in *E. coli* was grown on 25 cm×25 cm plates containing 200 ml LB agar supplemented with 100 µg/ml ampicillin added. Nearly confluent colonies were scraped from plates in 10 ml of cold TS solution (50 mM Tris, pH 8.0 and 10% Sucrose(w/v)). A 2.0 ml aliquot of 10 mg/ml lysozyme made in 0.25M Tris, pH 8.0 was added; then 8 ml of 0.25M ethylenediamine tetraacetic acid (EDTA) was added. The mix was inverted several times and incubated on ice for 10 minutes. A 4 ml aliquot of a 10% SDS solution was added slowly while mixing gently with a glass rod. Next, 6.0 ml of 5M NaCl was added slowly while mixing with a glass rod. The cell lysate was incubated on ice for 1 hour and then centrifuged. The supernatant was saved and then extracted twice with an equal volume of Tris-saturated Phenol/Chloroform (50:50). DNA was precipitated by adding 2 volumes of ethanol, freezing at –70° C. for 15 minutes and then centrifuging at 3,000 rpm for 15 minutes. The precipitated cosmid DNA was dried and resuspended in 9 ml of Tris-EDTA.

Cosmid DNA was prepared for cesium chloride density gradient purification by dissolving 10 gm of $CsCl_2$ in the DNA suspension and then adding 250 µl of 10 mg/ml ethidium bromide. Cosmid DNA was banded with a 20 hour centrifugation in a Ti865.1 Sorvall rotor at 55,000 rpm. The DNA bands representing cosmid DNA were recovered from the gradient, and ethidium bromide was removed by extraction with water-saturated butanol. Cosmid DNA was precipitated by adding 3 volumes of water and 10 volumes of ethanol, incubating on ice for 30 minutes and then centrifuging. The DNA was resuspended in Tris-EDTA and reprecipitated by the addition of 0.1 volume of 3M sodium acetate and 2.5 volumes of ethanol. DNA was frozen at –70° C. for 10 minutes, centrifuged, and resuspended in Tris-EDTA.

The DNA preparation was electrophoresed through a 0.5% Low Melting Temperature Agarose (BioRad) gel to eliminate contamination by pLO9 DNA. The band containing cosmid DNA with inserts was cut from the gel and heated to 65° C. with 2 volumes of Tris-EDTA. The melted agarose was extracted 3 times with Tris-saturated phenol and then once with chloroform. Cosmid library DNA was precipitated by addition of 0.1 volumes of 3M sodium acetate and 2.5 volumes of ethanol, freezing at –70° C. for 15 minutes, and centrifuging at 10,000 rpm for 15 minutes. The DNA was dried and resuspended in Tris-EDTA. The concentration of DNA was determined by measuring the optical density at 260 nm.

EXAMPLE 7

Transformation of *A. terreus*

Cultures were grown by inoculating $1 \times 10^8$ conidiospores into 50 ml of CM media in a 250 ml Erlenmeyer flask. Cultures were grown for between 24 and 30 hr at 200 rpm and 28° C. Mycelia were harvested by gravity filtration through Miracloth. Mycelia (4 g) were transferred to a 500 ml Erlenmeyer flask containing 100 ml KMP. KMP consists of 700 mM KCl, 800 mM Mannitol, and 20 mM $KH_2PO_4$ pH 6.3. Lysing Enzymes from *Trichoderma harzianum* (100 mg; Sigma) was added. Flasks were shaken at 100 rpm for 18 hours at 28° C.

Spheroplasts were harvested by gravity filtration through Miracloth. The filtrate was collected in 50 ml conical centrifuge tubes, concentrated by centrifugation and washed by resuspending the spheroplasted cells in 15 ml of KCM solution. KCM consists of 700 mM KCl; 10 mM MOPS adjusted to pH 5.8. The washing was repeated twice. Washed spheroplasts were resuspended at a concentration of $5 \times 10^7$/ ml in KCMC. KCMC consists of 5% 1M $CaCl_2$ and 95% KCM.

For each transformation, a sample of 5 µg of DNA was brought to a volume of 20 µl in Tris-EDTA; then 5 units of heparin in 6.5 µl of KCMC was added. Next, 200 µl aliquot of the spheroplast suspension was added to the DNA-containing solution. Finally, 50 µl of aliquot of a solution containing 5% 1M $CaCl_2$ and 95% PCMC (40% PEG 8,000; 10 mM MOPS, pH 5.8; 0.05M $CaCl_2$) was added. The mixture was incubated on ice for 30 minutes.

An aliquot (600 µl) of the KCMC solution was added to a 45° C. equilibrated solution of MA. MA consists of 5% Clutterbuck's salts(v/v); 0.5% Tryptone (w/v); 0.5% Yeast Extract (w/v); 1.0% Glucose(w/v); 23.4% Mannitol(w/v) and 3% Agar. This suspension was divided among 5 pre-weighed petri dishes and incubated at 28° C. for 4 hours. The weight of agar in each plate was determined by a second weight and an equal amount of Overlay (OL) consisting of: 1% Peptone (w/v); 1% Agar (w/v); with between 100 µg/ml and 150 µg/ml (strain ATCC 20542) of phleomycin was added to each petri dish. Petri dishes were incubated at 28° C. and 65% humidity for 7–10 days before transformed colonies were picked.

EXAMPLE 8

Rescue of Cosmid DNA from *A. terreus*

The transforming cosmid DNA was rescued from an *A. terreus* transformants by isolating chromosomal DNA and packaging into lambda phage particles. Isolation of genomic DNA and packaging into lambda phage were performed as described above.

EXAMPLE 9
Detection of Lovastatin

Fermentation extracts were prepared by adding two volumes of reagent alcohol to the fermentation flasks and shaking the flasks were shaken for 15 minutes at 220 rpm and 28° C. The contents were allowed to settle for 15 minutes and 1 ml of the liquid was removed. The sample was diluted 1/20 in methanol, filtered and then analyzed by HPLC. Lovastatin was detected by a Waters HPLC using a 8 mm×10 cm C18 4 um Waters Novapak column. Mobile phases were A: Acetonitrile with 0.02% Trifluoroacetic acid and B: Distilled water with 0.02% Trifluoroacetic acid. Gradients were run at a flow rate of 1.5 ml/min. Initial conditions were 35% A and 65% B and were held for 1 minute after sample injection. A gradient was formed to 65% A and 35% B over 3 minutes and held for 3.6 minutes. Lovastatin ammonium salt was detected at 239 nm.

EXAMPLE 10
Southern Analysis of DNA

Southern analysis was performed by electrophoresing 5 µg of digested DNA on a 1.0% agarose gel in TAE buffer (0.04M Tris and 0.002M EDTA). DNA in the gel was denatured by soaking the gel in Solution A (1.5M NaCl and 0.5M NaOH) for 30 minutes. The gel was then neutralized in Solution B (1.0M Tris and 1.5M NaCl) for 30 minutes. DNA was transferred to nitrocellulose or nylon membranes by blotting overnight with a 10×SCC solution. SSC consists of 8.75% NaCl (w/v) and 4.4% sodium citrate (w/v), pH 7.0. DNA was baked onto the nitrocellulose at 80° C. under vacuum for 30 minutes.

Standard hybridization conditions were as described in Sambrook, J. et al. (Molecular Cloning, 1989 (ed. Chris Nolan) Cold Spring Harbor Press). Membranes were prepared for hybridization by incubating at 42° C. in hybridization buffer consisting of: 6×SSC, 5×Denhardt's reagent, 0.5% SDS, 100 µg/ml denatured and fragmented salmon sperm DNA, and 40% formamide. After incubating for two hours, the denatured labeled probe was added and further incubated overnight at 42° C. Unless otherwise stated, the filters were washed twice in 6×SSC and 0.1% SDS at room temperature for 15 minutes followed by two 30 minute washes at 42° C. in 0.1×SSC and 0.5% SDS. Filters were exposed to X-ray film for visualization of the signal.

EXAMPLE 11
A. Isolation of Triol Polyketide Synthase from *A. terreus*

Mycelia of *A. terreus* were grown in GP-9 medium. After 48 hours the mycelia were collected by vacuum filtration, washed with cold water, frozen in liquid nitrogen and lyophilized. All subsequent steps of the purification were performed on ice or at 3° C. unless otherwise noted.

Lyophilized mycelia (6 g) were homogenized by grinding with 20 gm glass beads (0.2 mm) in a mortar with pestle in 135 ml homogenization buffer consisting of: 20 mM Tris, pH 8; 10% glycerol; 5 mM EDTA; 50 mM NaCl; 5 mM ascorbic acid; 3.8 µg/ml leupeptin; 17.7 µg/ml chymostatin; 2.0 µg/ml pepstatin, 42 µg/ml turkey trypsin inhibitor; 0.2 mM PMSF; and 2.2% (dry wt/v) hydrated polyvinyl polypyrrolidone. The homogenate was centrifuged at 7,650×g for 10 minutes; and the supernatant applied to an SH-affinity column (Affi-gel 501 organomercurial agarose; Bio-Rad; 1.5×8.0 cm) equilibrated in Buffer A. Buffer A consists of 20 mM Tris, pH 8; 50 mM NaCl; 5 mM EDTA; 5 mM ascorbic acid; at 30 ml/hr. The column was washed with 25 ml Buffer A followed by 75 ml Buffer A containing 0.5M NaCl. After reequilibrating the column with 50 ml Buffer A, bound proteins were eluted with 40 ml Buffer A supplemented with 100 mM dithiothreotol (DTT). The eluted protein fraction was made 4.2 µg/ml leupeptin; 2 µg/ml pepstatin; 18 µg/ml chymostatin; 0.2 mM PMSF and then was pelleted by ultracentrifugation at 180,000×g for 16 hr. The supernatant was discarded, and the pellet was rinsed with a buffer consisting of 20 mM Tris, pH 8; 5 mM ascorbic acid; 1 mM DTT; 1 mM EDTA. The washed pellet was resuspended in 2 ml of buffer consisting of 40 mM Tris, pH 6.8; 20 mM DTT; 2% SDS, then heated to 0° C. for 10 minutes and put on ice.

A 250 µl aliquot of the resuspended pellet was combined with an equal volume of sample buffer (125 mM Tris, pH 6.8; 20% glycerol; 0.005%(w/v) bromphenol blue; 4%(w/v) SDS; 1.5M beta mercaptoethanol) and heated to 95° C. for 10 minutes. The sample was electrophoresed on a preparative 1.5 mm, 4% acrylamide SDS precast gel (Novex) at 145V for 2 hr using Laemmeli electrode buffer system (25 mM Tris; 192 mM glycine; 0.1% SDS). When a prestained 200 kD reference standard was 1.4 cm from the bottom of the gel, the electrophoresis was terminated.

Proteins were visualized as follow. The gel was rinsed for 5 seconds in distilled $H_2O$, then rinsed for 10 minutes in 0.2M imidazole with shaking and was then transferred to a solution of 0.3M zinc acetate for 5 minutes with shaking. The gel was then rinsed in water. The TPKS, which ran with an apparent molecular weight of 235 kD, was localized to a relative mobility position of 0.53 (relative to the bottom of the gel). The TPKS protein was the protein of greatest abundance on the gel; no significant protein banding was seen with lower $R_f$. The apparent 235 kD protein band was excised from the gel and was then destained in 0.25M Tris and 0.25M EDTA pH 9.5 for approximately 5 minutes.

The destained gel slice was crushed between two glass plates and placed in a 50 ml tube containing 5 ml of 20 mM Tris, 5 mM EDTA, 0.1% SDS, pH 8.0. The tube was shaken on a rotary shaker for 48 hours at 37° C. Gel fragments were removed by centrifugation, and the supernatant containing the eluted protein was concentrated to 100 µl with a Centricon 30 microconcentrator (Amicon).

B. Molecular Weight Determination

The gel-purified protein was resuspended in Laemmli load buffer, heated to 95° C. for 5 min. and then electrophoresed on a 4–15% gradient SDS polyacrylamide gel (BioRad Ready-Gel) in Laemmli electrode buffer. After staining, the molecular weight of the protein was determined by comparison to molecular weight standard proteins.

C. Antibody Production

The TPKS protein was prepared via preparative SDS-PAGE as described, except the protein was not electroeluted from the acrylamide gel matrix. Following destaining, the gel slice was crushed between two glass plates, and first forced through a 18 gauge syringe needle and then through a 25 gauge syringe needle. A 0.5 ml aliquot of the 25 gauge needle eluate was mixed with an equal volume of Freund's complete adjuvant and injected intradermally at five sites of a New Zealand white male rabbit. Boosts were done at 21 and 42 days using protein prepared as described, but mixed with 0.5 ml of Freund's incomplete adjuvant. Ten days after the final boost the rabbit was exsanguinated and the antiserum collected.

D. Affinity Purification of Antibody

Affinity purified antibody was prepared by immobilizing the TPKS protein to PVDF membrane by transfer from a preparative SDS polyacrylamide gel. The TPKS was visualized and that area of the membrane cut out. After blocking in 5%(w/v) non-fat dry milk in TTBS for 1 hour, the membrane was washed 3×5 minutes in TTBS. A 2 ml aliquot of antisera was diluted 1:1 with TTBS supplemented with 1%(w/v) non-fat dry milk and incubated with the immobilized antigen for 5 hours. The membrane was then washed 4×(10 minutes per wash) with TTBS, and the bound antibody was eluted with 2 ml of 0.1M glycine, pH 2.8. The eluted antibody was neutralized with 50 µl of 1.0M Tris, pH 9.5 and concentrated twenty-fold.

E. Western Blot Analysis

Purified TPKS protein and partially purified protein preparations of organomercurial eluates were resolved by 4% acrylamide SDS-PAGE (NOVEX, precast 1.0 mm thick gels) and then transferred to nitrocellulose in Towbin transfer buffer (25 mM Tris; 192 mM glycine, pH 8.3; 20% methanol; 0.05% SDS) at 240 mA for 2 hr. All subsequent steps were done at room temperature with shaking.

The nitrocellulose blot was rinsed for 1 minute in TBS (50 mM Tris, pH 7.5; 0.5M NaCl) and then blocked for 2 hours in TBS supplemented with 0.05% Tween 20 (TTBS) and 5%(w/v) non-fat dry milk. The blot was incubated with the primary antibody (a 1:1000 dilution of rabbit antisera in TTBS containing 1%(w/v) non-fat dry milk) for 16 hr. The blot was washed in TTBS 3 times for 5 min. The blot was incubated with the second antibody (goat anti-rabbit alkaline phosphatase conjugate diluted 1:1000) for 2 hr in TTBS supplemented 1%(w/v) non-fat dry milk. After washing 4 times (10 minutes per wash) in TTBS, color development was achieved with 5-bromo-4-chloro-3-indolyl phosphate (115 µg/ml) and nitroblue tetrazolium (330 µg/ml) in 66 mM Tris, pH 9.5; 0.1M NaCl; 5 mM $MgCl_2$.

EXAMPLE 12
Isolation of Aspergillus RNA
A. Isolation of Total RNA

A. terreus was grown for 48 hours in 25 ml of GP-9 fermentation medium at 28° C. and 220 rpm on a rotary shaker. Mycelia were collected by vacuum filtration through Miracloth and cheesecloth and washed with approximately 100 ml distilled water. The mycelia were scraped from the filter into a plastic beaker and frozen with liquid nitrogen. Frozen mycelia were stored at −80° C. until needed.

Frozen mycelia were weighed and placed in a mortar chilled with liquid nitrogen. Approximately 2 g of 0.2 mm glass beads were added, and the mix was ground to a fine powder with a pestle. Liquid nitrogen was added as needed to keep the mycelia frozen at all times. Ground mycelia were added to a flask containing approximately 2.5 ml/g Breaking Buffer (50 mM Tris pH 7.4; 150 mM NaCl; 5 mM EDTA; 5% SDS(w/v)) and an equal volume of Tris-saturated phenol:chloroform:isoamyl alcohol (50:50:1), and vanadyl ribonucleoside complex (BRL) to a final concentration of approximately 2 mM. The mixture incubated on a rotary shaker at 37° C. for 20 minutes and was then centrifuged at 12000×g for 10 min at 4° C. The aqueous layer was removed and extracted with an equal volume of Tris-saturated phenol:chloroform:isoamyl alcohol (50:50:1). Second and third extractions were done with 1M Tris-saturated phenol:chloroform (50:50) and chloroform, respectively. The final aqueous layer was mixed with an equal volume of 6M LiCl and left at −20° C. for at least 4 hours. The precipitate was pelleted at 12,000×g for 20 minutes at 4° C. and resuspended in 0.6 ml water treated with 0.1% diethyl pyrocarbonate (DEPC). The total RNA was reprecipitated with 0.1 volume of sodium acetate and 2.5 volumes ethanol. The final pellet was dissolved in 0.3 ml water treated with 0.1% DEPC.

B. Isolation of Polyadenylated RNA

Polyadenylated RNA was isolated by heating approximately 500 µg of total RNA in 0.2 to 1.0 ml water to 65° C. for 5 minutes, cooling on ice, and adding 10×sample buffer consisting of: 10 mM Tris pH 7.5; 1 mM EDTA; 5M NaCl in 0.1% DEPC-treated water to a final concentration of 1×. The treated sample was applied to a column of oligod(T) cellulose prepared according to the manufacturer's instructions (Poly(A)Quik™ mRNA purification kit—Stratagene). The column was washed twice with High Salt Buffer (10 mM Tris pH 7.5; 1 mM EDTA; 0.5M NaCl) and three times with Low Salt Buffer (10 mM Tris pH 7.5; 1 mM EDTA and 0.1M NaCl). PolyA mRNA was then eluted from the column with four 200 µl aliquots of Elution Buffer (10 mM Tris pH 7.5 and 1 mM EDTA) which had been heated to 65° C. RNA concentration was determined spectrophotometrically using absorbance at 260 nm.

EXAMPLE 13
Construction of Lambda gt-11 cDNA Library

A cDNA library was constructed using 4 to 5 µg of polyadenylated RNA that had been purified twice over an oligo(dT) column. The reagents for construction of cDNA, addition of adapters and ligation of lambda gt-11 arms except [$^{32}$P]dCTP were provided in the Superscript™ Choice System (BRL) and were used according to the manufacturer's instructions.

First strand synthesis was primed using either 0.05 µg random hexamers plus 0.5 µg oligo(dT)12–18 or 1 µg oligo(dT)12–18 alone. The reaction was carried out in a final volume of 20 µl (final composition: 50 mM Tris, pH 8.3; 75 mM KCl; 3 mM $MgCl_2$; 10 mM DTT; 500 uM each dATP, dCTP, dGTP, dTTP; primers; mRNA; 10 µCi [$^{32}$P]dCTP; 200 U Superscript™ reverse transcriptase/µg mRNA). The reaction mixture was incubated for 1 hr at 37° C. and then placed on ice.

Second strand synthesis was carried out in a final volume of 150 µl using 18 µl of the first strand reaction. The final composition of the reaction was: 25 mM Tris pH 7.5; 100 mM KCl; 5 mM $MgCl_2$; 10 mM $(NH_4)_2SO_4$; 0.15 mM B-NAD+; 250 µM each dATP, dCTP, dGTP, dTTP; 1.2 mM DTT; 65 U/ml DNA Ligase; 250 U/ml DNA polymerase I; and 13 U/ml RNase H. This reaction mixture was incubated at 16° C. for 2 hr; then 10 U of T4 DNA polymerase was added, and the incubation was continued at 16° C. for an additional 5 minutes. The reaction was put on ice and stopped by adding 10 µl of 0.5M EDTA. The mix was extracted with 150 µl of Tris-saturated phenol:chloroform:isoamyl alcohol (25:24:1). The aqueous layer was removed, and cDNA was precipitated with 0.5 volume 7.5M ammonium acetate and 3.5 volumes ethanol. The cDNA pellet was washed with 70% ethanol. EcoRI (Not1) adapters were ligated to the cDNA in a reaction mix comprised of 66 mM Tris, pH 7.6; 10 mM $MgCl_2$; 1 mM ATP; 14 mM DTT; 200 µg/ml EcoRI (Not1) adapters; 100 U/ml T4 DNA ligase. The reaction mixture was incubated for 16 hours at 16° C., then heated to 70° C. and placed on ice. The adapted cDNA was phosphorylated by adding 30 U of T4 polynucleotide kinase to the reaction mix and incubating for 30 minutes at 37° C. The kinase was inactivated by heating to 70° C. for 10 minutes. The completed reaction was diluted with 97 µl of TEN buffer (10 mM Tris, pH 7.5; 0.1 mM EDTA; 25 mM NaCl) and placed over a Sephacryl® DNA sizing column prepared according to the manufacturer's directions (BRL). The DNA was eluted with TEN buffer and fractions were collected. Cerenkov counts were obtained for each fraction and the amount of cDNA/fraction was calculated. The column fractions were pooled in order of elution until 50 ng cDNA was collected. The pool was then precipitated with 5 µl yeast tRNA, 0.5 volumes 7.5M ammonium acetate and 2 volumes ethanol (−20° C.). The resultant pellet was washed with 70% ethanol, dried and ligated to lambda gt-11 arms. The final composition of the ligation reaction was 50 mM Tris pH 7.6; 10 mM MgCl$_2$; 1 mM ATP; 5% PEG 8000(w/v); 1 mM DTT; 100 µg/ml lambda vector EcoRI turns; 10 µg/ml cDNA; and 200 U/ml T4 DNA ligase. This mixture was incubated for 3 hours at room temperature. The cDNA/lambda gt-11 ligation was packaged into infectious lambda phage particles as described above.

EXAMPLE 14

A. Antibody Screening of Lambda gt-11 Library

E. coli strain Y1090 was used as the host for lambda phage infections and was maintained on LB/ampicillin plates consisting of: 1% tryptone (w/v); 0.5% yeast extract (w/v); 0.5% NaCl (w/v); 1.5% agar (w/v); the pH was adjusted to 7.5 before autoclaving, and 100 µg/ml ampicillin added after autoclaving. Cultures were grown for phage infection by incubating a single colony overnight on a rotary shaker at 37° C. in 3 ml LB/maltose broth consisting of: 1% tryptone(w/v); 0.5% yeast extract(w/v); 0.5% NaCl(w/v) and 0.2% maltose(w/v).

B. Pretreatment of Antisera

Antisera were treated with an E. coli lysate prior to screening so as to decrease cross-reaction to E. coli protein. E. coli lysate was prepared from Y1090 cells grown overnight in LB broth at 37° C. on a rotary shaker at 220 rpm. Cells were pelleted by centrifugation at 10,000×g at 4° C. and resuspended in 3 ml Lysate Buffer (50 mM Tris pH 8.0 and 10 mM EDTA). Cells were frozen in a dry ice/ethanol bath and thawed at room temperature; the freeze/thaw process was repeated. The suspension was sonicated 5×10 seconds at output control 4 on a constant duty cycle using a Branson Sonifier 450. Cells were placed on ice for 10 seconds after each pulse. Protein concentration in the lysate was estimated using the Bradford Assay (Bio-Rad) according to the manufacturer's suggestion. Sonicated lysate was stored at −20° C. until needed. The antisera was diluted 10-fold with TBST plus 1% dried milk(w/v) and mixed with 1/20 volume E. coli lysate. This solution was incubated at room temperature on a rotary shaker for two hours.

C. Screening of Lambda Gt-11 Phage Plaques

Recombinant phage diluted to 6×10$^3$ pfu in 100 µl of SM was added to 600 µl of an overnight culture of E. coli Y1090 and absorbed at 37° C. for 30 minutes. The cells were then added to 7.5 ml of a 47° C. solution of LB Top Agarose/MgSO$_4$ (0.1% tryptone(w/v); 0.5% yeast extract(w/v); 0.5% NaCl(w/v); 10 mM MgSO$_4$) and plated on a 140 mm LB agar plate. The plate was incubated at 42° C. for approximately 5 hours until tiny plaques were visible. The plate was then overlaid with a 137 mm nitrocellulose filter which had been saturated with a 10 mM solution of IPTG (isopropyl-B-D-thiogalactopyranoside) and air-dried. Incubation of the plate was continued overnight at 37° C. The filter was removed and washed 3 times for 15 minutes each. All washes were carried out at room temperature on a rotary shaker in TBST. The filters were blocked in TBST plus 5% w/v dried milk (Carnation instant non-fat dried milk) for 30 minutes at room temperature on a rotary shaker. Filters were washed 3×15 minutes and then incubated with a 1:1000 dilution of goat anti-rabbit IgG alkaline phosphatase conjugate (Bio-Rad) in TBST plus 1% dried milk(w/v) for 2 hours. The filters were washed 3×15 minutes and then developed in AP buffer (100 mM Tris pH 9.5; 100 mM NaCl; 5 mM MgCl$_2$) to which was added NBT (nitroblue tetrazolium) to a final concentration of 0.33 mg/ml and BCIP (5-bromo-4-chloro-3-indoyl phosphate) to a final concentration of 0.165 mg/ml for 2–5 minutes. The color reaction was stopped by washing the filters with water. Positive plaques were picked to 1 ml SM plus 10 µl chloroform and stored at 4° C. until needed.

Positive plaques were further purified until all the plaques on a filter were positive. Purification rounds were done on 100 mm LB/agar plates with phage titer adjusted to approximately 100 pfu/plate. Positive plaques were confirmed by screening with an affinity-purified antibody at a dilution of 1:100.

EXAMPLE 15

Preparation of Lambda DNA

Phage were adsorbed to 1.5 ml of an overnight culture of E. coli Y1090 at a multiplicity of infection of 0.01 for 30 minutes at 37° C. and then added to 300 ml LB media. The cells were incubated at 37° C. on a rotary shaker about 6 hours (until the cells lysed). One ml chloroform was added to complete the lysis. Cell debris was pelleted by centrifugation at 10,000×g for 10 minutes at 4° C. Lysate was stored at 4° C. until needed.

Lysate was treated with DNase I (final concentration 1 µg/ml) and RNase H (final concentration 5 µg/ml) at 37° C. for one hour. Phage were pelleted by centrifugation for 90 minutes at 27,000 rpm in a Sorvall AH-629 rotor; and the tubes were inverted to drain. Phage pellets were resuspended in 200 µl 0.05M Tris, pH 8 and were extracted with 200 µl Tris-saturated phenol by vigorous shaking for 20 minutes. The mixture was spun in a microcentrifuge, and the aqueous layer saved. The aqueous layer was extracted with phenol and then extracted twice with 200 µl chloroform. DNA was precipitated with 0.1 volume 3M sodium acetate and 6 volumes ethanol at room temperature. DNA was pelleted in a microcentrifuge, washed with 70% ethanol, dried and resuspended in 100 µl TE pH 8.0 (10 mM Tris; 1 mM EDTA).

EXAMPLE 16

Screening of EMBL3 Genomic Library

The EMBL3 genomic library was plated for screening with $^{32}$P-labeled DNA probes. Approximately 10,000 plaques were plated and transferred to nitrocellulose for hybridizations. Filters were prehybridized for 2 hours and hybridized overnight in hybridization buffer in the presence of a DNA probe labeled with $^{32}$P-dCTP (Oligolabeling Kit, Pharmacia). For the selection of EMBL-1, the DNA probe consisted of the EcoRI cDNA insert of lambda gt-11 2–9 which was identified using the antibody to the 235 kD protein. Filters were washed using the protocol employed for Southern hybridizations, and positive plaques were identified after an overnight exposure to film. DNA from positive EMBL-3 phage was prepared as described.

EXAMPLE 17

Sequencing Strategy and Analysis

A series of overlapping subclones from the genomic EMBL1 clone, which contained the triol PKS gene, were constructed in M13mp18 and M13mp19. Nested deletions of some of the clones were obtained using the Cyclone I Biosystem (International Biotechnologies, Inc., New Haven, Conn.). Single stranded DNA was purified by precipitation with 20% polyethylene glycol-2.5M NaCl followed by phenol extraction and ethanol precipitation. The nucelotide sequence of both strands of the DNA was determined using the USB Sequenase Version 2.0 DNA Sequencing Kit (United States Biochemicals, Cleveland, Ohio). The −40 sequencing primer from the kit or custom synthesized oligonucleotides were used to prime the reactions. Regions containing GC compressions were resequenced using dITP in place of dGTP. The sequencing reactions were separated on 6% polyacrylamide denaturing gels. The genomic M13 clones were resequenced using a 373A DNA Sequencer (Applied Biosystems, Inc.) for verification. Introns were identified by sequence analysis of cDNA. The RNA was prepared from a 16 hr culture grown in GP9 medium, and cDNA was synthesized using AMV reverse transcriptase. Custom synthesized oligonucleotides were used to amplify short overlapping stretches of the cDNA by PCR. The PCR conditions, reagents, and product purification were performed as described for PCR with genomic DNA in the PCR/Sequencing Kit PCR Amplification Module manual (Applied Biosystems, Inc., Foster City, Calif.). The PCR were performed using a Perkin Elmer GeneAmp PCR system 9600. The PCR products were sequenced as described in the Taq DyeDeoxy Terminator Cycle Sequencing Kit manual (Applied Biosystems, Inc.), and sequencing reactions were analyzed using the 373A DNA Sequencer. All sequence analyses and manipulations were performed using GeneWorks (IntelliGenetics, Inc., Mt. View, Calif.) on a Macintosh computer (Apple Computer, Inc., Cupertino, Calif.).

EXAMPLE 18

A. Construction of pTPKS100

The transformation vector pTPKS100 contains the polyketide synthase gene responsible for the synthesis of the nonaketide backbone of the triol structure, the phleomycin resistance gene for selection in *A. terreus* and the ampicillin resistance gene for selection in *E. coli*.

The vector was constructed from the pUT715 vector (Cayla, Toulouse Cedex, France) which contains the phleomycin resistance marker from *S. hindustanus* and the termination sequence from the Cyc1 gene in *S. cerevisiae*. The pUT715 vector was digested with BamHI and EcoRv. The β-tubulin gene promoter was inserted in front of the phleomycin marker gene as follows. The β-tubulin promoter was removed from pTL113 by digestion with EcoRI, filling with Klenow fragment, and releasing the fragment from the vector with a BglII digest. The β-promoter was ligated into the pUT715 vector to form pCLS7. The β-tubulin promoter, phleomycin marker and Cyc1 terminator were removed from PCLS7 by digestion with NdeI and BglII followed by filling in the sites, and ligating into the SmaI site of the Bluescript vector (Strategene). This vector was named pLOA.

The polyketide synthase gene was inserted into pLOA in a two step process. The promoter and 5'-end of the PKS gene was obtained from EMBL-1 as a KpnI to EcoRI fragment and ligated into pLOA which had been digested with KpnI and EcoRI. This vector was named TPKS A. The 3' end of the PKS gene was then added to the construction by digesting TPKS A with EcoRI and ligating in the 3' EcoRI gene fragment isolated from EMBL-1. The resulting vector was named pTPKS100.

Transformation of a lovastatin-nonproducing strain with pTPKS100 restored lovastatin production. Transformation of ATCC 20542 (a lovastatin-producing strain) increased lovastatin production relative to untransformed cells.

EXAMPLE 19

Transformation of *A. terreus* ATCC 20542

To determine whether increasing the copy number of the PKS gene in a lovastatin-producing strain would result in an increase in the amount of lovastatin produced, a set of experiments were designed and carried out using the *A. terreus* ATCC 20542. ATCC 20542 was transformed with pTPKS-100. Transformants were checked by PCR to confirm that they contained the phleomycin marker and were true transformants. Following single spore isolation, the confirmed transformants were fermented and lovastatin production was measured by HPLC. The highest producer of single isolates, strain 3-17-7#7, was 32% greater for the transformant than for the parent.

EXAMPLE 20

Characterization of the TPKS Protein Sequence

Splicing of the introns from the DNA sequence and translation of the 9114 nucleotide open reading frame results in a protein of 3038 amino acids with a molecular weight of 269,090 daltons. The final amino acid sequence of the TPKS protein is shown in FIGS. 2A–2C. The features discussed below are are presented with their amino acid position noted in the following table.

| TPKS PROTEIN FEATURES | | |
|---|---|---|
| Description | Motif | Amino Acid |
| Keto-acyl synthase | Cysteine | 181 |
| Acetyl/Malonyl Transferase | GXSXG | 654–658 |
| Dehydratase | HXXXGXXXXP | 985–994 |
| Methyl Transferase | GXGXG | 1446–1450 |
| Enoyl Reductase | SXGXXS | 1932–1937 |
| Keto Reductase | LXGXXG | 2164–2169 |
| Acyl Carrier Protein | Serine | 2498 |

Inspection of the TPKS amino acid sequence for active site residues and motifs known to be associated with polyketide synthases and fatty acid synthase (FAS) activities resulted in the identification of candidates for expected functional sites. These sites were identified by carrying out searches for amino acid sequences and amino acid homologies using the Intelligenetics Gene Works program. A graphic view of the open reading frame of the protein and the overall placement of the TPKS peptide sequences obtained by partial sequence analysis of TPKS peptides and PKS activities established by alignments and is shown in the figures. Except for the presence of a methyl transferase, not present in FAS, the succession of activities on the TPKS protein is the same as that observed for the rat FAS protein. The alignments carried out on regions of the TPKS, the rat FAS, and the 6-methylsalicyclic acid synthase (6-MSAS) of *Penicillium patulin* in order to identify the best candidate for each of the activities are also presented in the figures.

EXAMPLE 21

Identification of the Keto Acyl Synthase Region

The most 5' site is the β-keto acyl synthase (KAS), also known as the condensing enzyme. This activity is centered around the active site cysteine to which the acyl chain is attached prior to the entry and condensation of the incoming acyl unit. The region shown in the Keto Acyl Synthase Alignment figure contains 30% homology when compared to both the rat FAS and 6-MSAS sequences. However, the TPKS KAS region is most closely related to the rat FAS sequence, exhibiting 49% homology over this region compared to 41% to 6-MSAS.

EXAMPLE 22

Identification of the Acetyl Malonyl Transferase

Proceeding towards the COOH terminus, the next functional site identified is the acetyl/malonyl transferase, which is responsible for accepting the incoming substrate for transfer to either the active thiol of the beta-keto synthase (if a priming acetyl unit) or to the active site thiol of the ACP-pantetheine-SH if a malonyl building block. The identification of the acetyl/malonyl transferase site was found by searching for the GXSXG motif found in many proteins with an active site serine (Wakil, S. J., 1989, Biochemistry 28: 4523–4530). The conservation of this motif in the TPKS protein was observed beginning at amino acid 654, as shown in the figures.

EXAMPLE 23
Identification of the Dehydratase

The next site in common with the FAS protein is the dehydratase. The dehydratase motif consistently found not only in the rat FAS, but the 6-MSAS and the erythromycin SU4 as well consist of a "HXXXGXXXXP" sequence (Donadio, S. and Katz, L., 1992, Gene 111, 51–60.). The homology outside of this signature sequence is very weak.

EXAMPLE 24
Identification of the Enoyl and Keto Reductase

The next two activities identified on the rat FAS protein are the enoyl reductase (ER) and keto reductase (KR). In general, the ER and KR are identified by searching for the GXGXXG/A motif which is proposed to represent the pyridine nucleotide binding site in many proteins (Wierenga, R. K. and Hol, W. G. J., 1983, Nature 302, 842–844). An identical match to this motif has been identified in the rat FAS for both the KR and ER (Witkowski, V., et. al., 1991, Eur. J. Biochem. 198, 571–579). Inspection of the TPKS protein identified three matches to the motif. The first begins at position 321 between the β-keto synthase and acetyl/malonyl transferase functions. However, this is not considered to be a good candidate for either of the reductase activities due to its 5' position in the protein and because it lies in a region which is highly homologous to rat FAS. The GXGXXG motif is seen again at position 1446–1451, however, this is considered to be part of the methyl transferase domain. The third time the motif occurs is at position 2438 which lies 60 amino acids 5' of the ACP active site serine. A similar GXGXXG motif is seen in the rat FAS at 125 amino acids prior to the ACP and in 6-MSAS 129 amino acids 5' of the ACP. Since candidates for the NAD(P) binding sites of the KR and ER were not observed in the TPKS protein, homology searches were performed between the regions of the rat FAS which contain these sites and similar regions of the TPKS protein.

As shown in the Enoyl Reductase Alignment, the region of the TPKS protein which lies between the dehydratase and the keto reductase and shows the best alignment to the rat FAS enoyl reductase does not bear a strong homology to the GXGXXG motif or to the region in general. A much stronger homology is evident between the ER domain of SU4 of Erythromycin AII and the rat FAS sequence. The Keto Reductase Alignment of the rat FAS and 6-MSAS keto reductase regions with the TPKS shows slightly higher homology, with 6 out of 30 amino acids surrounding the glycine-rich region conserved between all genes and 13 of 30 conserved between TPKS and either FAS or 6-MSAS.

The glycine-rich segment is part of an overall structural motif for pyridine-nucleotide binding domains in many proteins (Wierenga, ibid.; Scrutton, N. S., et. al., 1990, Nature 343, 38–43; Ma, Q., et. al., 1992, 267, 22298–22304; Hanukoglu, I., and Gutfinger, T., 1989 Eur J. Biochem. 180 479–484). This structural motif consists of a beta sheet-turn-alpha helix where the glycine rich region codes for the strong turn signal in the middle. In addition, downstream acidic or basic amino acids are positioned to bind to the phosphate (NADP) or hydroxyl group (NAD) on the 2' ribose position. This is depicted in a Chou Fasman analysis of the secondary structure of horse alcohol dehydrogenase as a model NADP binding protein. The analysis of the structural characteristics using the Chou Fasman algorithm indicate that this structural motif is conserved in the rat FAS ER and KR domains, (Witkowski, A., 1991, Eur. J. Biochem. 198, 571–579). The structural predictions of the amino acid sequence of the TPKS ER and KR, as well as the 6MSAS KR, show variations of the model. All predicted structures show a β sheet leading into a turn region, even when amino acid homologies are not strong. It has been suggested that deviations from the structural model may reflect differences in substrate specificity (Ma, Q., supra). It is possible that these structural variations are important in the programming of the PKS, resulting in different levels of reduction of the beta-keto group during successive cycles of the biosynthesis of the triol precursor. Consistent throughout the alignments are the presence of basic amino acids at position 20 to 23 amino acids from the "glycine rich" regions identified by the homology searches. The structural similarities and the presence of these basic amino acids suggest that these regions do indeed represent the keto and enoyl reductases of the TPKS protein.

EXAMPLE 25
Identification of the Acyl Carrier Protein

The last active site identified by alignment of the rat FAS with the TPKS is the acyl carrier protein (ACP) active site serine which binds the 4'-phosphopantetheine prosthetic group. While only 6 out of 30 amino acids surrounding the active site serine are conserved over TPKS, rat FAS and 6-MSAS, a higher degree of homology (13 of 30 amino acids) is observed between TPKS and either rat FAS or 6-MSAS.

EXAMPLE 26
Identification of the Methyl Transferase

One activity identified within the reading frame of the TPKS protein which is not present in rat FAS is the methyl transferase responsible for transfer of the methyl group from S-adenosylmethionine (SAM) to the polyketide chain at position 6. A comparison of both eucaryotic and procaryotic methyl transferases responsible for the methylation of RNA, DNA, and protein substrates has identified a sequence motif thought to be part of the SAM-binding domain (Ingrosso, D. et. al., 1989, J. Biol. Chem., 264, 20131–20139; Wu, G. et. al., 1992, J. Gen. Micro, 138, 2101–2112). The binding motif and its alignment with the proposed methyl transferase of the TPKS are shown in the figures.

The absence of a methyl group in compactin suggests that the methyl transferase domain may be absent or altered in the compactin PKS.

EXAMPLE 27
A. Transformation of *Monascus ruber*

Cultures of *M. ruber* strains M4681 AND M82121 are grown, spheroplasted and transformed essentially according to the procedures described above. Petri dishes are incubated at 28° C. and 65% humidity for 7–10 days before transformed colonies are picked.

B. Fermentation of Monascus

The transformed cultures are grown aerobically in a medium containing 7% glycerol, 3% glucose, 3% meat extract, 0.8% peptone, 0.2% $NaNO_3$, and 0.1% $MgSO_4 \cdot 7H_2O$ at 25 degrees C. for 10 days (Kimura et al., 1990. *Biosyn. of Monacolins, Conversion of Monacolin J. To Monacolin K (Mevinolin)*, J. of Antibiotics, Vol. XLIII No. 12, 1621–1622). M. ruber M82121 is grown aerobically at 25° C. for 11 days in a medium containing 11% glycerol, 1% glucose, 5% soy bean powder, 0.8% peptone, 0.1% $NaNO_3$, 0.05% $Zn(NO_3)_2$, and 0.5% olive oil (pH 6.5) (Endo, et al. *Dihydromonacolin L and Monacolin X. New Metabolites Those Inhibit Cholesterol Biosynthesis*, J. Antibiot. Vol. XXXVIII No. 3, 321–327). The culture broth is extracted with a solvent such as methanol or dichloromethane, concentrated amd analyzed by methods such as HPLC. By comparison with an untransformed host or a *M. ruber* culture containing pL09 without the TPKS genes, the TPKS 100 containing host or a derivative thereof produces increased levels of lovastatin, triol, monacolin, dihydromonacolin L or monacolin X.

EXAMPLE 28

A. Transformation of *Paecilomyces viridis*

*P. viridis* strain L-63 is grown, spheroplasted and transformed essentially according to the procedures described above. Cells are transformed with pTPKS100 or a derivative thereof. An example of such a derivative is one in which the DNA encoding the methyl transferase activity of the TPKS protein is altered such that an active methyl transferase is not produced. Petri dishes are incubated at 28° C. and 65% humidity for 7–10 days before transformed colonies are picked.

B. Fermentation of Paecilomyces

*P. viridis* L-63 is grown aerobically in a medium containing 7% glycerol, 3% glucose, 3% meat extract, 0.8% peptone, 0.2% $NaNO_3$, and 0.1% $MgSO_4.7H_2O$ at 25° C. for 4 to 10 days (Kimura et al., supra) The culture broth is extracted with a solvent such as methanol or dichloromethane and concentrated by evaporation if necessary. By comparison with an untransformed host or a *P. viridis* culture containing pLOA without the TPKS genes, the transformed host can be shown to ferment increased levels of ML-236A and compactin.

EXAMPLE 29

A. Transformation of *Penicillium citrinum*

A suitable culture of *P. citrinum* (e.g.,Nara, et al. 1993. *Development of a transformation system for the filamentous. ML-236B (compactin)—producing fungus Penicillium citrinum*. Curr Genet. 23: 28–32) is transformed with pTPKS100 or an appropriate derivative thereof using conventional methods.

B. Fermentation of *P.citrinum*

The transformed culture is maintained on yeast-malt extract agar slant (4 g/l dextrose, 10 g/l malt extract, 4 g/l yeast extract, agar 20 g/l, pH 7 prior to sterilization). The slant is washed and used to inoculate to flasks containing KF seed medium (10 g/l $CaCl_2$, 5 g/l corn steep liquor, 40 g/l tomato paste, 10 g/l oatmeal, 10 g/l cerelose, 10 ml trace element per liter, pH 6.8; trace elements consist of 1 g $FeSO_4.7H_2O$ 1 g $MnSO_4.4H_2O$, 25 mg $CuCl_2.2H_2O$, 100 mg $CaCl_2$, 56 mg $H_3BO_3$, 19 mg $(NH_4)_6Mo7O24.H_2O$, 200 mg $ZnSO_4.7H_2O$ in liter of $dH_2O$). The KF seed flasks are incubated for about 3 days at about 28° C. and 220 rpm. Approximately 1.5 ml is used to inoculate 40 ml of LM production medium per 250 ml flask. LM medium contains 20 g/l dextrose, 20 ml/l glycerol, 10 g/l ardamine pH, 20 g/l malt extract, 8 mg/l $CoCls.6H_2O$ and 0.25% polyglycol P2000, pH 7.0. After 5 to 10 days at 25° C. on a shaker, the broth is collected, extracted and concentrated. The transformed culture produces more compactin and dihydrocompactin than does the untransformed parent culture.

EXAMPLE 30

Cloning of TPKS cDNA into a Mammalian Expression Vector

TPKS cDNA expression cassettes are ligated at appropriate restriction endonuclease sites to the following vectors containing strong, universal mammalian promoters:

Cassettes containing the TPKS cDNA in the positive orientation with respect to the promoter are ligated into appropriate restriction sites 3' of the promoter and identified by restriction site mapping and/or sequencing. These cDNA expression vectors are introduced into various host cells by standard methods including but not limited to electroporation, or chemical procedures (cationic liposomes, DEAE dextran, calcium phosphate). Transfected cells and cell culture supernatants can be harvested and analyzed for TPKS expression as described below.

Vectors used for mammalian transient expression may be used to establish stable cell lines expressing TPKS.

EXAMPLE 31

Cloning of TPKS cDNA into a Baculovirus Expression Vector for Expression in Insect Cells Baculovirus vectors, which are derived from the genome of the AcNPV virus, are designed to provide high level expression of cDNA in the Sf9 line of insect cells. Recombinant baculoviruses expressing TPKS cDNA are produced essentially by by standard methods (InVitrogen Maxbac Manual). The TPKS cDNA constructs are ligated into the polyhedrin gene in a variety of baculovirus transfer vectors including but not limited to pAC360 and the BlueBac vector (InVitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Following plaque purification, TPKS expression is measured by the assays described above.

Authentic, enzymatically-active TPKS is found in the cytoplasm of infected cells. Active TPKS is extracted from infected cells under native conditions by hypotonic or detergent lysis.

EXAMPLE 32

Cloning of TPKS cDNA into a yeast expression vector

Recombinant TPKS is produced in the yeast *S. cerevisiae* following the insertion of the optimal TPKS cDNA cistron into expression vectors designed to direct the intracellular or extracellular expression of heterologous proteins. In the case of intracellular expression, vectors such as EmBLyex4 or the like are ligated to the TPKS cistron [Rinas, U. et al., Biotechnology 8: 543–545 (1990); Horowitz B. et al., J. Biol. Chem. 265: 4189–4192 (1989)]. For extracellular expression, the TPKS cistron is ligated into yeast expression vectors which fuse a secretion signal (a yeast or mammalian peptide) to the $NH_2$ terminus of the TPKS protein [Jacobson, M. A., Gene 85: 511–516 (1989); Riett L. and Bellon N. Biochem. 28: 2941–2949 (1989)].

EXAMPLE 33

Use of TPKS for in vitro production of HMG-CoA inhibitors

Recombinant proteins, including complex proteins, can be overexpressed in a heterologous cells (e.g., Roberts et al., 1993, Heterologous expression in *E. coli* of an intact multienzyme component of the erythromycin-producing polyketide synthase. Eur J. Biochem 214; 305–311) If the recombinant protein is produced in an inclusion body, renaturation of the desired protein is carried out prior to enzymatic assay (Roberts, 1993).

A suitable host cell is transformed with a vector encoding the TPKS gene. The transformed host cell is grown under conditions that permit the expression of TPKS. The expressed TPKS is isolated and partially purified. The recovered active TPKS enzyme can be added to a reaction mixture containing acetyl-CoA or other charged acyl compounds, appropriate cofactors, and buffer. Incubation of the system can result in the formation of HMG-CoA reductase inhibitors.

EXAMPLE 34

Cloning of other PKS genes using TPKS gene

The cross hybridization of the DNA representing portions of the TPKS gene to genomic DNA isolated from other organisms such as *M. ruber* or *P. citrinum*, makes it possible to clone the homologous genes from the parent organisms. To do this, a genomic library of *M. ruber* or *P. citrinum* was constructed from genomic DNA according to conventional methods. Using, for example, an EMBL vector, an EMBL genomic library was prepared, plated and screened by hybridization with a $^{32}$P-labeled DNA probe consisting of the PstI fragment from the TPKS gene. The PstI fragment contains the keto synthase sequence of the gene. Positive plaques were selected and subjected to additional screening until a purified cross-reacting plaque was selected. The DNA contained in the positive clone is further characterized by physical methods such as restriction mapping, Southern hybridization and DNA sequencing. The function of the defined gene is characterized by cloning the gene in an appropriate transformation vector and transforming a lovastatin non-producing strain with the vector. In the case of *M. ruber*, the cross-reacting PKS would be expected to restore production of Monacolin K (lovastatin) while introduction of a functional *P. citrinum* PKS would result in production of compactin.

EXAMPLE 35

Homology of *A. terreus* TPKS to other strains

A large segment of the 5' end of the *A. terreus* TPKS gene containing the keto synthase region was used to look for cross-hybridization of this region to other strains, including *M. ruber*, *P. citrinum* and *P. brevicompactum*. The homology was examined by Southern analyses with two probes. The Southern showed cross-reaction to all three strains.

The first probe was the PstI fragment, an 800 bps probe which spans the KAS active site. This probe contains intron I 5' of the active site cysteine in addition to the entire KAS region. This probe was used to detect homology in all three strains. *A. terreus* displayed the profile of cross-reacting bands expected from the restriction map. *M. ruber*, another lovastatin-producing organism, and *P. citrinum*, a compactin-producing organism, showed different but strong hybridizations to the probe.

The second probe was a synthetic oligonucleotide probe having the following sequence:
5'GATACGGCATGCAGCTCGTCGTTGGT-TGCCGTTCATCTGGCTGCA3' (SEQ ID NO:3) Although the hybridization signal to this probe was weaker than the hybridization to the first probe, the results confirm the observations made with the PstI fragment.

When a 3' end cDNA probe was used, cross reaction to all three strains was observed. Single cross-reacting bands in many of the digests indicate that only one gene is being detected in the genomic DNA of each strain. These data suggest that *M. ruber* and *P. citrinum* contain a gene with substantial homology to the TPKS gene of *A. terreus*.

EXAMPLE 36

Use of mutagenized TPKS

The DNA encoding TPKS is mutagenized using standard methods to produce an altered TPKS gene. Host cells are transformed with the altered TPKS to produce altered triol polyketides or altered polyketides with therapeutic use. The altered TPKS protein may be isolated and purified

What is claimed is:

1. Purified DNA encoding triol polyketide synthase from a microorganism selected from the group consisting of *Monascus ruber* and *Penicillum citrinum*.

2. An expression vector comprising the DNA molecule of claim 1.

3. A host cell transformed with the expression vector of claim 2.

4. A process for producing HMG-CoA reductase inhibitors, comprising:

(a) transforming a cell with the DNA molecule of claim 1;

(b) cultivating the transformed cell under conditions that permit the expression of the DNA molecule; and (c) recovering the HMG-CoA reductase inhibitor.

5. The process of claim 4 wherein the HMG-CoA reductase inhibitors are selected from the group consisting of lovastatin, triol and compactin.

6. The process of claim 5 wherein and transformed cell is selected from the group consisting of *Aspergillus terreus, Monascus ruber, Penicillum citrinum, Penicillum brevicompactum, Hypomyces chrysospermus, Paecilomyces viridis* L-63 *Paecilomyces sp.* M2016, *Eupenicillium sp.* MM603, *Trichoderma longibrachiatum* M6735 and *Trichoderma pseudokoningii* M6828.

\* \* \* \* \*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 11561 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( v i ) ORIGINAL SOURCE:
      ( A ) ORGANISM: TPKS cDNA ( x i ) SEQUENCE DESCRIPTION: SEQ ID NO:1:

```
CTGCAGTCAA  CGGATCACTT  ACCATTGCTG  TCGCCAAAAA  TATCCGTGAT  AATCCCGCTG      60

GCTTCATTGG  CAAGAGGCTT  GACGTACTTG  GGAGCTTGGG  TCTGGAACTG  GTTCATAACC     120

ACCTTGGTGA  TGAGATGTGC  ATCCCTCGTG  ACTTCCTTGA  ATCCATCGAA  TCCGGGAAGA     180

TGAGAGTGAA  AGTCCTGATG  AGAGCACGAA  GATCAGTAAG  TCAGGTCCTC  ACAGCGGAAG     240

CAGTTGCAAA  GAACGGTGGA  CTCCTTACCG  TGCCCAAGAA  CTTGTACATA  CAGAGCTCTT     300
```

```
TCATCTTGCG AAACTCATCG GCCATAGAGG AGGGAAGAAT GGTGCAGTAC CCAGAGTCGA    360
CTATGAACCG AATGGGCTTA TCATTTGCG  AGAACCAGCT CTCAATCCAT GACGGTGCAT    420
TCGCATCAAA ATCCCGTTTG GCCCTCATGG TCGTCAGTTC CCACCATGTT TTCGGATTGA    480
ACACCGGCAG ATCAGATCTC CGGCCACTCG AGCACAGGTA AAGAAGAAGG CATAGTAGCC    540
CCGCACTGGT AGTGACCAAG GGCGCAAACC ACGAGCCATG TTGCTGCGTG TCATTCCAAG    600
CCAGCGACAG AAGGTGGTGC GGCTGTGTGA GCGCGTCGAC AGTCATGGCT AGGAGACCAG    660
GTGTGGTTGA GGGATAAGAT ATCGAGAGTG ATGTGAGCAA AAGATCCGGG AAAGGTCGCG    720
AAGGAAAGGG CGTCTCTCTT ACCAAGAAAG TCTGTTCCCT ATCATGCAAT CACCGCTTGC    780
TGTACGGTGG TGATGATGCT GGGATGGTGG TGGGTCCCCA CCGAATAACG CCGGACAGCT    840
GTTGAAGCCG AATGACGCCG GCAGGCCAAA AGAACCCTAC CTTCACTTAC TCAATCGGCG    900
CTTCCCCTCC TATCACCAAA TCGGATGTAA ATGGACGGGC CTTAATAGCG ACCGGCCGGG    960
CCGGGAATCC CCAAACGTAG ATAGATAGGC ATAGACCCGA AATCTTTGGC CCGGCATACA   1020
TGAGCACAGG AAGTTTCACG CGACGGCGCC TTTCCTGCCT CAGCTTCAAT CCAAGCTCAC   1080
GAGTTCTGTC GCCTCTATCA GTCGTGCAAT TGTCCTACTG CAAACAGCAT GGCTCAATCT   1140
ATGTATCCTA ATGAGCCTAT TGTCGTGGTC GGCAGTGGTT GTCGCTTCCC TGGTGACGCC   1200
AACACACCCT CCAAGCTCTG GGAGCTACTC CAGCATCCTC GCGATGTGCA GAGTCGAATC   1260
CCCAAAGAAC GATTTGACGT CGACACATTT TATCACCCGG ACGGGAAGCA CCACGGGCGA   1320
ACAAATGCAC CCTACGCCTA TGTTCTCCAA GACGATCTGG GCGCCTTCGA TGCGGCCTTC   1380
TTCAATATCC AGGCTGGAGA GGCCGAGAGT ATGGACCCCC AGCACCGGCT GTTGCTGGAG   1440
ACGGTGTACG AGGCCGTAAC GAATGCTGGA ATGCGTATCC AGGATCTGCA GGAACTTCG    1500
ACTGCTGTTT ACGTCGGGGT GATGACGCAC GACTATGAGA CTGTCTCAAC CCGCGACCTG   1560
GAGAGCATCC CCACCTACTC GGCGACGGGT GTCGCGGTCA GTGTTGCGTC CAACCGCATC   1620
TCGTATTTTT TTGACTGGCA TGGACCAAGT GTAAGTCACC CAATATCGTG TAGCAGTCTA   1680
ATCATGCTCT AACGGACCGG GATGGTTGAA AGATGACGAT CGATACGGCA TGCAGCTCGT   1740
CGTTGGTTGC CGTTCATCTG GCGGTGCAAC AGCTACGGAC GGGTCAAAGC TCCATGGCAA   1800
TTGCTGCGGG TGCGAATCTG ATTCTGGGGC CCATGACATT CGTCCTTGAA AGCAAATTGA   1860
GCATGCTATC CCCCTCGGGT CGATCCCGCA TGTGGGACGC CGGAGCTGAC GGCTATGCCA   1920
GAGGCGTGAG TGTTTCTTGA GCTCGTAGAT GACAGTTCCC ATCGCTGACC GTGATCAGGA   1980
AGCTGTTTGC TCTGTAGTGT TGAAGACATT GAGTCAAGCC TTGCGCGATG GGACACGAT    2040
TGAATGTGTC ATCCGAGAAA CTGGGGTGAA TCAAGATGGC CGAACGACCG GAATTACGAT   2100
GCCGAACCAT AGTGCTCAGG AGGCACTCAT CAAGGCTACC TACGCCCAGG CTGGCCTTGA   2160
CATCACCAAG GCCGAGGACA GGTGCCAATT CTTCGAGGCT CATGGTCAGC AAAGAGAACC   2220
TGTTCTGTTG GCGCCCTGCA GCTGACATTC GTATGATAGG GACTGGTACT CCGGCCGGAG   2280
ATCCCAGGA  GGCGGAGGCC ATTGCAACAG CCTTCTTCGG CCACGAGCAG GTAGCACGCA   2340
GCGACGGAAA CGAGAGGGCC CCTCTGTTCG TGGGCAGTGC GAAAACTGTT GTCGGGCACA   2400
CCGAGGGCAC GGCCGGTCTG GCTGGTCTCA TGAAGGCGTC GTTCGCTGTC CGCCATGGGG   2460
TAATCCCCCC CAACCTGCTG TTCGACAAAA TCAGCCCGCG AGTCGCCCCA TTCTATAAAA   2520
ACCTGAGGAT TCCGACAGAA GCTACCCAAT GGCCAGCTCT CCCACCCGGA CAACCGCGCC   2580
GCGCCAGTGT CAACTCCTTT GGTAAGCGAG GATTGCCCGG AGGAACCCTC ACAAGTACTC   2640
GAATTAATGC TAACTGAACC GCGCCGATGG ACAGGATTCG GCGGCACGAA TGCGCATGCC   2700
```

```
ATTATTGAGG AATACATGGA GCCAGAGCAA AACCAGCTGC GAGTCTCGAA TAATGAGGAC    2760
TGCCCACCCA TGACCGGTGT CCTGAGTTTA CCCTTAGTCC TCTCGGCGAA GTCCAGCGC     2820
TCCTTAAAGA TAATGATGGA GGAGATGCTG CAATTCCTTC AGTCTCACCC CGAGATACAC    2880
TTGCACGACC TCACCTGGTC CTTACTGCGC AAGCGGTCAG TTCTACCCTT CCGCCGGGCT    2940
ATTGTCGGCC ATAGTCATGA AACCATCCGC CGGGCTTTGG AGGATGCCAT CGAGGATGGT    3000
ATTGTGTCGA GCGACTTCAC TACGGAGGTC AGAGGCCAGC CATCGGTGTT GGGAATCTTC    3060
ACCGGGCAGG GGGCGCAGTG GCCGGGGATG TTAAAGAATC TGATAGAGGC ATCGCCATAT    3120
GTGCGGAACA TAGTGAGGGA GCTGGACGAC TCCCTGCAGA GCTTGCCGGA AAAATACCGG    3180
CCCTCGTGGA CGCTACTGGA CCAGTTCATG CTAGAAGGAG AGGCCTCCAA CGTCAATAT    3240
GCTACTTTCT CCCAGCCATT ATGCTGCGCG GTGCAAATTG TCCTGGTCCG TCTCCTTGAA    3300
GCCGCGAGAA TACGATTCAC GGCTGTTGTT GGACATAGCT CCGGCGAAAT TGCTTGCGCC    3360
TTTGCTGCCG GGCTCATCAG TGCCTCGTTG GCGATTCGGA TTGCTTACTT ACGTGGAGTC    3420
GTCTCGGCAG GGGGCGCCAG AGGCACACCG GAGCCATGT TGGCCGCCGG GATGTCCTTT    3480
GAGGAAGCAC AAGAGATCTG CGAGTTGGAT GCCTTTGAGG GCCGCATCTG CGTGGCTGCC    3540
AGCAATTCCC CAGACAGTGT AACTTTCTCT GGCGACGCGA ACGCAATTGA TCACCTGAAG    3600
GGCATGTTGG AGGATGAGTC CACTTTTGCG AGACTGCTCA AGGTCGATAC AGCGTACCAC    3660
TCGCATCATA TGCTTCCATG TGCAGACCCA TATATGCAAG CCCTAGAAGA GTGTGGTTGT    3720
GCTGTTGCCG ATGCAGGTTC CCCAGCCGGA AGTGTACCCT GGTATTCGTC CGTGGACGCC    3780
GAGAACAGGC AAATGGCAGC AAGAGACGTG ACCGCCAAGT ACTGGAAAGA TAACTTAGTA    3840
TCTCCGGTGC TATTCTCCCA CGCAGTGCAG CGGGCAGTCG TCACGCACAA GGCGCTGGAT    3900
ATCGGGATTG AAGTGGGCTG TCACCCAGCT CTCAAGAGCC CATGCGTCGC CACCATCAAG    3960
GATGTCCTAT CTGGGGTTGA CCTGGCGTAT ACAGGTTGCT TGGAGCGAGG AAAGAATGAT    4020
CTCGATTCAT TCTCTCGAGC ACTGGCATAT CTCTGGGAAA GGTTTGGTGC CTCCAGTTTC    4080
GATGCGGACG AGTTCATGCG TGCAGTCGCG CCTGATCGGC CCTGTATGAG TGTGTCGAAG    4140
CTCCTACCGG CCTATCCATG GGACCGCTCT CGTCGCTACT GGGTGGAATC CCGAGCAACT    4200
CGCCACCATC TTCGAGGGCC CAAGCCCCAT CTTCTATTAG GAAAGCTCTC CGAATACAGC    4260
ACTCCGCTAA GCTTCCAGTG GCTGAATTTT GTGCGCCCAC GAGACATTGA ATGGCTTGAT    4320
GGACATGCAT TGCAAGGCCA GACTGTCTTC CCTGCGGCCG GCTATATCGT CATGGCAATG    4380
GAAGCAGCCT TAATGATTGC TGGCACCCAC GCAAAGCAGG TCAAGTTACT GGAGATCTTG    4440
GATATGAGCA TTGACAAGGC GGTGATATTT GACGACGAAG ACAGCTTGGT TGAGCTCAAC    4500
CTGACAGCTG ACGTGTCTCG CAACGCCGGC GAAGCAGGTT CAATGACCAT AAGCTTCAAG    4560
ATCGATTCCT GTCTATCGAA GGAGGGTAAC CTATCCCTAT CAGCCAAGGG CCAACTGGCC    4620
CTAACGATAG AAGATGTCAA TCCCAGGACG ACTTCCGCTA GCGACCAGCA CCATCTTCCC    4680
CCGCCAGAAG AGGAACATCC TCATATGAAC CGTGTCAACA TCAATGCTTT CTACCACGAG    4740
CTGGGGTTGA TGGGGTACAA CTACAGTAAG GACTTCCGGC GTCTCCATAA CATGCAACGA    4800
GCAGATCTTC GAGCCAGCGG CACCTTAGAC TTCATTCCTC TGATGGACGA GGGTAATGGC    4860
TGTCCTCTCC TGCTGCATCC TGCATCATTG GACGTCGCCT TCCAGACTGT CATCGGCGCA    4920
TACTCCTCCC CAGGTGATCG GCGTCTACGC TGTCTGTATG TACCCACTCA CGTTGATCGC    4980
ATCACACTTG TCCCATCCCT TTGCCTGGCA ACGGCTGAGT CCGGATGCGA GAAGGTTGCC    5040
TTCAATACTA TCAATACGTA CGACAAGGGA GACTACTTGA GCGGTGACAT TGTGGTGTTT    5100
```

-continued

```
GACGCGGAGC AGACCACCCT GTTCCAGGTT GAAAATATTA CTTTTAAGCC CTTTTCACCC      5160
CCGGATGCTT CAACTGACCA TGCGATGTTT GCCCGATGGA GCTGGGGTCC GTTGACTCCG      5220
GACTCGCTGC TGGATAACCC GGAGTATTGG GCCACCGCGC AGGACAAGGA GGCGATTCCT      5280
ATTATCGAAC GCATCGTCTA CTTCTATATC CGATCGTTCC TCAGTCAGCT TACGCTGGAG      5340
GAGCGCCAGC AGGCAGCCTT CCATTTGCAG AAGCAGATCG AGTGGCTCGA ACAAGTCCTG      5400
GCCAGCGCCA GGAGGGTCG TCACCTATGG TACGACCCCG GGTGGGAGAA TGATACTGAG       5460
GCCCAGATTG AGCACCTTTG TACTGCTAAC TCCTACCACC CTCATGTTCG CCTGGTTCAG      5520
CGAGTCGGCC AACACCTGCT CCCCACCGTA CGATCGAACG GCAACCCATT CGACCTTCTG      5580
GACCACGATG GGCTCCTGAC GGAGTTCTAT ACCAACACAC TCAGCTTCGG ACCCGCACTA      5640
CACTACGCCC GGGAATTGGT GGCGCAGATC GCCCATCGCT ATCAGTCAAT GGATATTCTG      5700
GAGATTGGAG CAGGGACCGG CGGCGCTACC AAGTACGTGT GGCCACGCC CCAGCTGGGG       5760
TTCAACAGCT ACACATACAC CGATATCTCC ACCGGATTCT TCGAGCAAGC GCGGGAGCAA      5820
TTTGCCCCCT TCGAGGACCG GATGGTGTTT GAACCCCTCG ATATCCGCCG CAGTCCCGCC      5880
GAGCAGGGCT TCGAGCCGCA TGCCTATGAT CTGATCATTG CCTCCAATGT GCTACATGCG      5940
ACACCCGACC TAGAGAAAAC CATGGCTCAC GCCCGCTCTC TGCTCAAGCC TGGAGGCCAG      6000
ATGGTTATTC TGGAGATTAC CCACAAAGAA CACACGGC TCGGGTTTAT CTTTGGTCTG        6060
TTCGCCGACT GGTGGGCTGG GGTGGATGAT GGTCGCTGCA CTGAGCCGTT TGTCTCGTTC      6120
GACCGCTGGG ATGCGATCCT AAAGCGTGTC GGGTTTTCCG GTGTGGACAG TCGCACCACG      6180
GATCGGGACG CAAATCTATT CCCGACCTCT GTGTTTAGTA CCCATGCAAT TGACGCCACC      6240
GTGGAGTACT TAGACGCGCC GCTTGCCAGC AGCGGCACCG TCAAGGACTC TTACCCTCCC      6300
TTGGTGGTGG TAGGAGGGCA GACCCCCCAA TCTCAGCGTC TCCTGAACGA TATAAAAGCG      6360
ATCATGCCTC CTCGTCCGCT CCAGACATAC AAGCGCCTCG TGGATTTGCT AGACGCGGAG      6420
GAGCTGCCGA TGAAGTCCAC GTTTGTCATG CTCACGGAGC TGGACGAGGA ATTATTCGCC      6480
GGGCTCACTG AAGAGACCTT CGAGGCAACC AAGCTGCTGC TCACGTACGC CAGCAATACG      6540
GTCTGGCTGA CAGAAAATGC CTGGGTCCAA CATCCTCACC AGGCGAGCAC GATCGGCATG      6600
CTACGCTCCA TCCGCCGGGA GCATCCTGAC TTGGGAGTTC ATGTTCTGGA CGTCGACGCG      6660
GTTGAAACCT TCGATGCAAC CTTCCTGGTT GAACAGGTGC TTCGGCTTGA GGAGCATACG      6720
GATGAGCTGG CCAGTTCAAC TACATGGACT CAAGAACCCG AGGTCTCCTG GTGTAAAGGC      6780
CGCCCGTGGA TTCCTCGTCT GAAGCGCGAT CTGGCTCGCA ATAACGAAT GAACTCCTCG       6840
CGCCGTCCCA TATACGAGAT GATCGATTCG TCGCGGGCTC CCGTGGCATT ACAGACGGCT      6900
CGGGATTCAT CATCCTACTT CTTGGAGTCC GCTGAAACCT GGTTTGTGCC TGAGAGTGTT      6960
CAGCAGATGG AAACAAAGAC GATCTATGTC CACTTTAGCT GTCCCATGC GCTTAGGGTC       7020
GGACAGCTCG GGTTTTTCTA TCTTGTGCAG GGTCACGTCC AGGAGGGCAA TCGCGAAGTG      7080
CCCGTCGTGG CCTTAGCAGA GCGTAACGCA TCCATTGTGC ACGTTCGTCC CGATTATATA      7140
TATACTGAGG CAGATAACAA TCTGTCTGAG GGTGGTGGCA GCCTTATGGT AACCGTCCTC      7200
GCCGCGGCGG TGTTGGCGGA GACGGTGATC AGTACCGCCA AGTGCCTGGG GGTAACTGAC      7260
TCAATCCTCG TTCTGAATCC CCCCAGCATA TGTGGGCAGA TGTTGCTCCA TGCTGGTGAA      7320
GAGATCGGTC TTCAAGTTCA TCTGGCCACC ACTTCTGGCA ACAGGAGTTC GGTTTCTGCT      7380
GGAGACGCCA AGTCCTGGCT AACATTGCAT GCTCGCGACA CGGACTGGCA CCTGCGACGG      7440
GTACTGCCCC GGGGTGTCCA GGCTTTAGTC GACTTATCAG CCGACCAGAG CTGTGAAGGT      7500
```

```
TTGACTCAGA GGATGATGAA AGTTCTGATG CCTGGCTGTG CCCATTACCG TGCGGCAGAC      7560
CTGTTCACAG ACACCGTTTC CACTGAATTG CATAGCGGAT CGCGGCATCA AGCTTCACTG      7620
CCCGCCGCAT ATTGGGAGCA TGTGGTATCC TTAGCCCGCC AGGGACTTCC TAGTGTCAGC      7680
GAGGGGTGGG AGGTGATGCC GTGCACTCAA TTTGCAGCGC ATGCCGACAA GACGCGCCCG      7740
GATCTCTCGA CAGTTATTTC CTGGCCCCGG GAGTCGGACG AGGCTACGCT TCCTACCAGG      7800
GTTCGCTCCA TTGACGCTGA GACCCTCTTT GCGGCCGACA AAACATATCT CCTGGTCGGA      7860
CTGACTGGAG ATCTTGGACG ATCACTAGGT CGTTGGATGG TCCAGCATGG GGCCTGCCAC      7920
ATTGTACTTA CGAGCAGAAA TCCGCAGGTG AACCCCAAGT GGCTGGCGCA TGTTGAAGAA      7980
CTGGGTGGTC GAGTCACTGT TCTTTCCATG TAAGAGGAGT CCTTCCTTCT GCAATTCCTC      8040
CTTATGATCC CGACTAACGC AGCTGGCTTC AGGGACGTGA CAAGCCAAAA CTCAGTGGAA      8100
GCTGGCCTGG CTAAACTCAA GGATCTGCAT CTGCCACCAG TGGGGGGTAT TGCCTTTGGC      8160
CCTCTGGTTC TGCAGGATGT GATGCTAAAT AATATGGAAC TGCCAATGAT GGAGATGGTG      8220
CTCAACCCCA AGGTCGAAGG CGTCCGCATC CTGCACGAGA AGTTCTCCGA TCCGACCAGT      8280
AGCAACCCTC TCGACTTCTT CGTGATGTTC TCCTCGATTG TGGCCGTCAT GGGCAACCCG      8340
GGTCAGGCTA ACTACAGTGC GGCTAACTGC TACCTTCAAG CGCTGGCGCA GCAGCGAGTT      8400
GCATCCGGAT TAGCAGTACG TTTTCACTCC ATCCTTTGCT AAACACTCCT ATGGGCCTTT      8460
ACTAAACCGG GCAGGCGTCC ACCATCGACA TCGGTGCCGT GTACGGCGTT GGGTTCGTCA      8520
CTCGGGCGGA GCTGGAGGAG GACTTTAATG CAATTCGGTT CATGTTCGAT TCGGTTGAGG      8580
AACATGAACT GCATACACTG TTTGCTGAGG CAGTGGTGGC CGGTCGACGA GCCGTGCACC      8640
AGCAAGAGCA GCAGCGGAAG TTCGCGACAG TGCTCGACAT GGCTGATCTG GAACTGACAA      8700
CCGGAATTCC GCCCCTGGAT CCAGCCCTCA AAGATCGGAT CACCTTCTTC GACGACCCCC      8760
GCATAGGCAA CTTAAAAATT CCGGAGTACC GAGGGGCCAA AGCAGGCGAA GGGGCAGCCG      8820
GCTCCAAGGG CTCGGTCAAA GAACAGCTCT TGCAGGCGAC GAACCTGGAC CAGGTCCGTC      8880
AGATCGTCAT CGGTAAGTTG AGCGAATCCG GGAATATTC TCCCCTTCCT CACTCAGCGG      8940
ACTGGAGATT AACCGCTTCT TTTCCTTTGG CAGATGGACT CTCCGCGAAG CTGCAGGTGA      9000
CCCTGCAGAT CCCCGATGGG GAAAGCGTGC ATCCCACCAT CCCACTAATC GATCAGGGGG      9060
TGGACTCTCT GGGCGCGGTC ACCGTGGGAA CCTGGTTCTC CAAGCAGCTG TACCTTGATT      9120
TGCCACTCCT GAAAGTGCTT GGGGGTGCTT CGATCACCGA TCTCGCTAAT GAGGCTGCTG      9180
CGCGATTGCC ACCTAGCTCC ATTCCCCTCG TCGCAGCCAC CGACGGGGGT GCAGAGAGCA      9240
CTGACAATAC TTCCGAGAAT GAAGTTTCGG GACGCGAGGA TACTGACCTT AGTGCCGCCG      9300
CCACCATCAC TGAGCCCTCG TCTGCCGACG AAGACGATAC GGAGCCGGGC GACGAGGACG      9360
TCCCGCGTTC CCACCATCCA CTGTCTCTCG GGCAAGAATA CTCCTGGAGA ATCCAGCAGG      9420
GAGCCGAAGA CCCCACCGTC TTTAACAACA CCATTGGTAT GTTCATGAAG GGCTCTATTG      9480
ACCTTAAACG GCTGTACAAG GCGTTGAGAG CGGTCTTGCG CCGCCACGAG ATCTTCCGCA      9540
CGGGGTTTGC CAACGTGGAT GAGAACGGGA TGGCCCAGCT GGTGTTTGGT CAAACCAAAA      9600
ACAAAGTCCA GACCATCCAA GTGTCTGACC GAGCCGGCGC CGAAGAGGGC TACCGACAAC      9660
TGGTGCAGAC ACGGTATAAC CCTGCCGCAG GAGACACCTT GCGGCTGGTG GACTTCTTCT      9720
GGGGCCAGGA CGACCATCTG CTGGTTGTGG CTTACCACCG ACTCGTCGGG GATGGATCTA      9780
CTACAGAGAA CATCTTCGTC GAAGCGGGCC AGCTCTACGA CGGCACGTCG CTAAGTCCAC      9840
ATGTCCCTCA GTTTGCGGAC CTGGCGGCAC GGCAACGCGC AATGCTCGAG GATGGGAGAA      9900
```

-continued

```
TGGAGGAGGA TCTCGCGTAC TGGAAGAAAA TGCATTACCG ACCGTCCTCA ATTCCAGTGC    9960
TCCCACTGAT GCGGCCCCTG GTAGGTAACA GTAGCAGGTC CGATACTCCA AATTTCCAGC   10020
ACTGTGGACC CTGGCAGCAG CACGAAGCCG TGGCGCGACT TGATCCGATG GTGGCCTTCC   10080
GCATCAAGGA GCGCAGTCGC AAGCACAAGG CGACGCCGAT GCAGTTCTAT CTGGCGGCGT   10140
ATCAGGTGCT GTTGGCGCGC CTCACCGACA GCACCGATCT CACCGTGGGC CTCGCCGACA   10200
CCAACCGTGC GACTGTCGAC GAGATGGCGG CCATGGGGTT CTTCGCCAAC CTCCTTCCCC   10260
TGCGCTTCCG GGATTTCCGC CCCCATATAA CGTTTGGCGA GCACCTTATC GCCACCCGTG   10320
ACCTGGTGCG TGAGGCCTTG CAGCACGCCC GCGTGCCCTA CGGCGTCCTC CTCGATCAAC   10380
TGGGGCTGGA GGTCCCGGTC CCGACCAGCA ATCAACCTGC GCCTTTGTTC CAGGCCGTCT   10440
TCGATTACAA GCAGGGCCAG GCGGAAAGTG GAACGATTGG GGGTGCCAAG ATAACCGAGG   10500
TGATTGCCAC GCGCGAGCGC ACCCCTTACG ATGTCGTGCT GGAGATGTCG GATGATCCCA   10560
CCAAGGATCC GCTGCTCACG GCCAAGTTAC AGAGTTCCCG CTACGAGGCT CACCACCCTC   10620
AAGCCTTCTT GGAGAGCTAC ATGTCCCTTC TCTCTATGTT CTCGATGAAT CCCGCCCTGA   10680
AGCTGGCATG ATGGCGCAAA CATAGAACAT GATAGCGCAG CAGGGACGAT GTAGATAGAG   10740
CTTTGCTTCT GCGGGTGGAT CTATAATATA GTATATATAA ATATGGTGAG CCGAACGAAG   10800
AGGGGGGAAT GCCACAATTA TTTACTGTTT GCGCCGTAC ACGAGGAGAA GACGTCCAGA   10860
ACAACATAAA TATATCACTC TAGTGAGACA CCATATATTC GGAGAGACTA TAAAAATATA   10920
CATCTACTCC AATGTCTGGG CCGTCACACA CAGCTTACGA AAACGATTAA TGACCTCCAA   10980
CACGTCGCGC GGTCGATTGG GAAACTGATG CTGCCCAGCA AACTCCAATA CCTGCGCCTC   11040
TCGGGGGGAG AAATGGCGCG CCACCAGCAT CTTCGATCCT GCGAGCGCAA AATCATCGCG   11100
ACCCTGCAGA TGTAATGTCG GTATCCGAAT GACCAGTTCC TCCTGCCACT CGGTATCTTT   11160
GCTGTCGTTG TCGTCGTCAT GGTTCTTCAT CATTCGTTCC TCATATACTG GCTTGCCTCG   11220
TCTTGATACC AGGGACAGAT CAACAGCGCA ACACTCATCC GGGGCAACCA GGGCAGGTGA   11280
CCCATCTGCT GCTGCCAGAG GAGCAAGGTC GTCACCAGGG CACCTTCGGA GAAACCGATA   11340
GCACCCACGA TAGGGATGTG GGGGTGTTGA GTCTGCCAGT CGACAATGGT GCGGCGGATG   11400
GGGTCGTGGA CGGCGGCGAG GCGTTCGCTC ACGGAGGGTC CATTATGATT GTTGTCGCTG   11460
CTGCTTTCAA ACCAGGAGTA ATATGGCCCT AGGTCGGCGA AGACGGGGAG AATCCCAGGC   11520
CCTGCAGAGG AAGGGAACGG AGCTGTCACG TAGACGAATT C                      11561
```

( 2 ) INFORMATION FOR SEQ ID NO:2:

( i ) SEQUENCE CHARACTERISTICS:
        ( A ) LENGTH: 3038 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( v i ) ORIGINAL SOURCE:
        ( A ) ORGANISM: TPKS Protein ( x i ) SEQUENCE DESCRIPTION: SEQ ID NO:2:

```
Met Ala Gln Ser Met Tyr Pro Asn Glu Pro Ile Val Val Val Gly Ser
1               5                   10                  15

Gly Cys Arg Phe Pro Gly Asp Ala Asn Thr Pro Ser Lys Leu Trp Glu
                20                  25                  30
```

```
Leu Leu Gln His Pro Arg Asp Val Gln Ser Arg Ile Pro Lys Glu Arg
         35                  40                  45
Phe Asp Val Asp Thr Phe Tyr His Pro Asp Gly Lys His His Gly Arg
     50                  55                  60
Thr Asn Ala Pro Tyr Ala Tyr Val Leu Gln Asp Asp Leu Gly Ala Phe
 65                  70                  75                   80
Asp Ala Ala Phe Phe Asn Ile Gln Ala Gly Glu Ala Glu Ser Met Asp
                 85                  90                   95
Pro Gln His Arg Leu Leu Leu Glu Thr Val Tyr Glu Ala Val Thr Asn
             100                 105                 110
Ala Gly Met Arg Ile Gln Asp Leu Gln Gly Thr Ser Thr Ala Val Tyr
         115                 120                 125
Val Gly Val Met Thr His Asp Tyr Glu Thr Val Ser Thr Arg Asp Leu
 130                 135                 140
Glu Ser Ile Pro Thr Tyr Ser Ala Thr Gly Val Ala Val Ser Val Ala
145                 150                 155                 160
Ser Asn Arg Ile Ser Tyr Phe Phe Asp Trp His Gly Pro Ser Met Thr
                 165                 170                 175
Ile Asp Thr Ala Cys Ser Ser Ser Leu Val Ala Val His Leu Ala Val
             180                 185                 190
Gln Gln Leu Arg Thr Gly Gln Ser Ser Met Ala Ile Ala Ala Gly Ala
         195                 200                 205
Asn Leu Ile Leu Gly Pro Met Thr Phe Val Leu Glu Ser Lys Leu Ser
 210                 215                 220
Met Leu Ser Pro Ser Gly Arg Ser Arg Met Trp Asp Ala Gly Ala Asp
225                 230                 235                 240
Gly Tyr Ala Arg Gly Glu Ala Val Cys Ser Val Val Leu Lys Thr Leu
                 245                 250                 255
Ser Gln Ala Leu Arg Asp Gly Asp Thr Ile Glu Cys Val Ile Arg Glu
             260                 265                 270
Thr Gly Val Asn Gln Asp Gly Arg Thr Thr Gly Ile Thr Met Pro Asn
         275                 280                 285
His Ser Ala Gln Glu Ala Leu Ile Lys Ala Thr Tyr Ala Gln Ala Gly
 290                 295                 300
Leu Asp Ile Thr Lys Ala Glu Asp Arg Cys Gln Phe Phe Glu Ala His
305                 310                 315                 320
Gly Thr Gly Thr Pro Ala Gly Asp Pro Gln Glu Ala Glu Ala Ile Ala
                 325                 330                 335
Thr Ala Phe Phe Gly His Glu Gln Val Ala Arg Ser Asp Gly Asn Glu
             340                 345                 350
Arg Ala Pro Leu Phe Val Gly Ser Ala Lys Thr Val Val Gly His Thr
         355                 360                 365
Glu Gly Thr Ala Gly Leu Ala Gly Leu Met Lys Ala Ser Phe Ala Val
 370                 375                 380
Arg His Gly Val Ile Pro Pro Asn Leu Leu Phe Asp Lys Ile Ser Pro
385                 390                 395                 400
Arg Val Ala Pro Phe Tyr Lys Asn Leu Arg Ile Pro Thr Glu Ala Thr
                 405                 410                 415
Gln Trp Pro Ala Leu Pro Pro Gly Gln Pro Arg Arg Ala Ser Val Asn
             420                 425                 430
Ser Phe Gly Phe Gly Gly Thr Asn Ala His Ala Ile Ile Glu Glu Tyr
         435                 440                 445
Met Glu Pro Glu Gln Asn Gln Leu Arg Val Ser Asn Asn Glu Asp Cys
```

-continued

|  |  |  | 450 |  |  |  |  |  | 455 |  |  |  | 460 |  |  |
|---|---|---|---|---|---|---|---|---|---|---|---|---|---|---|---|
| Pro 465 | Pro | Met | Thr | Gly | Val 470 | Leu | Ser | Leu | Pro 475 | Leu | Val | Leu | Ser | Ala | Lys 480 |
| Ser | Gln | Arg | Ser | Leu 485 | Lys | Ile | Met | Met | Glu 490 | Met | Leu | Gln | Phe 495 | Leu |  |
| Gln | Ser | His | Pro 500 | Glu | Ile | His | Leu | His 505 | Asp | Leu | Thr | Trp | Ser 510 | Leu | Leu |
| Arg | Lys | Arg 515 | Ser | Val | Leu | Pro | Phe 520 | Arg | Arg | Ala | Ile | Val 525 | Gly | His | Ser |
| His | Glu 530 | Thr | Ile | Arg | Arg | Ala 535 | Leu | Glu | Asp | Ala | Ile 540 | Glu | Asp | Gly | Ile |
| Val 545 | Ser | Ser | Asp | Phe | Thr 550 | Thr | Glu | Val | Arg | Gly 555 | Gln | Pro | Ser | Val | Leu 560 |
| Gly | Ile | Phe | Thr | Gly 565 | Gln | Gly | Ala | Gln | Trp 570 | Pro | Gly | Met | Leu | Lys 575 | Asn |
| Leu | Ile | Glu | Ala 580 | Ser | Pro | Tyr | Val | Arg 585 | Asn | Ile | Val | Arg | Glu 590 | Leu | Asp |
| Asp | Ser | Leu 595 | Gln | Ser | Leu | Pro | Glu 600 | Lys | Tyr | Arg | Pro | Ser 605 | Trp | Thr | Leu |
| Leu | Asp 610 | Gln | Phe | Met | Leu | Glu 615 | Gly | Glu | Ala | Ser | Asn 620 | Val | Gln | Tyr | Ala |
| Thr 625 | Phe | Ser | Gln | Pro | Leu 630 | Cys | Cys | Ala | Val | Gln 635 | Ile | Val | Leu | Val | Arg 640 |
| Leu | Leu | Glu | Ala | Ala 645 | Arg | Ile | Arg | Phe | Thr 650 | Ala | Val | Val | Gly | His 655 | Ser |
| Ser | Gly | Glu | Ile 660 | Ala | Cys | Ala | Phe | Ala 665 | Ala | Gly | Leu | Ile | Ser 670 | Ala | Ser |
| Leu | Ala | Ile 675 | Arg | Ile | Ala | Tyr | Leu 680 | Arg | Gly | Val | Val | Ser 685 | Ala | Gly | Gly |
| Ala | Arg 690 | Gly | Thr | Pro | Gly | Ala 695 | Met | Leu | Ala | Ala | Gly 700 | Met | Ser | Phe | Glu |
| Glu 705 | Ala | Gln | Glu | Ile | Cys 710 | Glu | Leu | Asp | Ala | Phe 715 | Glu | Gly | Arg | Ile | Cys 720 |
| Val | Ala | Ala | Ser | Asn 725 | Ser | Pro | Asp | Ser | Val 730 | Thr | Phe | Ser | Gly | Asp 735 | Ala |
| Asn | Ala | Ile | Asp 740 | His | Leu | Lys | Gly | Met 745 | Leu | Glu | Asp | Glu | Ser 750 | Thr | Phe |
| Ala | Arg | Leu 755 | Leu | Lys | Val | Asp | Thr 760 | Ala | Tyr | His | Ser | His 765 | His | Met | Leu |
| Pro | Cys 770 | Ala | Asp | Pro | Tyr | Met 775 | Gln | Ala | Leu | Glu | Glu 780 | Cys | Gly | Cys | Ala |
| Val 785 | Ala | Asp | Ala | Gly | Ser 790 | Pro | Ala | Gly | Ser | Val 795 | Pro | Trp | Tyr | Ser | Ser 800 |
| Val | Asp | Ala | Glu | Asn 805 | Arg | Gln | Met | Ala | Ala 810 | Arg | Asp | Val | Thr | Ala 815 | Lys |
| Tyr | Trp | Lys | Asp 820 | Asn | Leu | Val | Ser | Pro 825 | Val | Leu | Phe | Ser | His 830 | Ala | Val |
| Gln | Arg | Ala 835 | Val | Val | Thr | His | Lys 840 | Ala | Leu | Asp | Ile | Gly 845 | Ile | Glu | Val |
| Gly | Cys 850 | His | Pro | Ala | Leu | Lys 855 | Ser | Pro | Cys | Val | Ala 860 | Thr | Ile | Lys | Asp |
| Val 865 | Leu | Ser | Gly | Val | Asp 870 | Leu | Ala | Tyr | Thr | Gly 875 | Cys | Leu | Glu | Arg | Gly 880 |

```
Lys Asn Asp Leu Asp Ser Phe Ser Arg Ala Leu Ala Tyr Leu Trp Glu
            885                 890                 895
Arg Phe Gly Ala Ser Ser Phe Asp Ala Asp Glu Phe Met Arg Ala Val
        900                 905                 910
Ala Pro Asp Arg Pro Cys Met Ser Val Ser Lys Leu Leu Pro Ala Tyr
        915                 920                 925
Pro Trp Asp Arg Ser Arg Arg Tyr Trp Val Glu Ser Arg Ala Thr Arg
        930                 935                 940
His His Leu Arg Gly Pro Lys Pro His Leu Leu Leu Gly Lys Leu Ser
945                 950                 955                 960
Glu Tyr Ser Thr Pro Leu Ser Phe Gln Trp Leu Asn Phe Val Arg Pro
                965                 970                 975
Arg Asp Ile Glu Trp Leu Asp Gly His Ala Leu Gln Gly Gln Thr Val
            980                 985                 990
Phe Pro Ala Ala Gly Tyr Ile Val Met Ala Met Glu Ala Ala Leu Met
        995                 1000                1005
Ile Ala Gly Thr His Ala Lys Gln Val Lys Leu Leu Glu Ile Leu Asp
        1010                1015                1020
Met Ser Ile Asp Lys Ala Val Ile Phe Asp Glu Asp Ser Leu Val
1025                1030                1035                1040
Glu Leu Asn Leu Thr Ala Asp Val Ser Arg Asn Ala Gly Glu Ala Gly
                1045                1050                1055
Ser Met Thr Ile Ser Phe Lys Ile Asp Ser Cys Leu Ser Lys Glu Gly
                1060                1065                1070
Asn Leu Ser Leu Ser Ala Lys Gly Gln Leu Ala Leu Thr Ile Glu Asp
            1075                1080                1085
Val Asn Pro Arg Thr Thr Ser Ala Ser Asp Gln His His Leu Pro Pro
        1090                1095                1100
Pro Glu Glu Glu His Pro His Met Asn Arg Val Asn Ile Asn Ala Phe
1105                1110                1115                1120
Tyr His Glu Leu Gly Leu Met Gly Tyr Asn Tyr Ser Lys Asp Phe Arg
                1125                1130                1135
Arg Leu His Asn Met Gln Arg Ala Asp Leu Arg Ala Ser Gly Thr Leu
                1140                1145                1150
Asp Phe Ile Pro Leu Met Asp Glu Gly Asn Gly Cys Pro Leu Leu Leu
        1155                1160                1165
His Pro Ala Ser Leu Asp Val Ala Phe Gln Thr Val Ile Gly Ala Tyr
    1170                1175                1180
Ser Ser Pro Gly Asp Arg Arg Leu Arg Cys Leu Tyr Val Pro Thr His
1185                1190                1195                1200
Val Asp Arg Ile Thr Leu Val Pro Ser Leu Cys Leu Ala Thr Ala Glu
            1205                1210                1215
Ser Gly Cys Glu Lys Val Ala Phe Asn Thr Ile Asn Thr Tyr Asp Lys
        1220                1225                1230
Gly Asp Tyr Leu Ser Gly Asp Ile Val Val Phe Asp Ala Glu Gln Thr
        1235                1240                1245
Thr Leu Phe Gln Val Glu Asn Ile Thr Phe Lys Pro Phe Ser Pro Pro
        1250                1255                1260
Asp Ala Ser Thr Asp His Ala Met Phe Ala Arg Trp Ser Trp Gly Pro
1265                1270                1275                1280
Leu Thr Pro Asp Ser Leu Leu Asp Asn Pro Glu Tyr Trp Ala Thr Ala
                1285                1290                1295
Gln Asp Lys Glu Ala Ile Pro Ile Ile Glu Arg Ile Val Tyr Phe Tyr
            1300                1305                1310
```

Ile Arg Ser Phe Leu Ser Gln Leu Thr Leu Glu Glu Arg Gln Gln Ala
1315                 1320                 1325

Ala Phe His Leu Gln Lys Gln Ile Glu Trp Leu Glu Gln Val Leu Ala
        1330                 1335                 1340

Ser Ala Lys Glu Gly Arg His Leu Trp Tyr Asp Pro Gly Trp Glu Asn
1345                 1350                 1355                 1360

Asp Thr Glu Ala Gln Ile Glu His Leu Cys Thr Ala Asn Ser Tyr His
                1365                 1370                 1375

Pro His Val Arg Leu Val Gln Arg Val Gly Gln His Leu Leu Pro Thr
            1380                 1385                 1390

Val Arg Ser Asn Gly Asn Pro Phe Asp Leu Leu Asp His Asp Gly Leu
    1395                 1400                 1405

Leu Thr Glu Phe Tyr Thr Asn Thr Leu Ser Phe Gly Pro Ala Leu His
    1410                 1415                 1420

Tyr Ala Arg Glu Leu Val Ala Gln Ile Ala His Arg Tyr Gln Ser Met
1425                 1430                 1435                 1440

Asp Ile Leu Glu Ile Gly Ala Gly Thr Gly Gly Ala Thr Lys Tyr Val
                1445                 1450                 1455

Leu Ala Thr Pro Gln Leu Gly Phe Asn Ser Tyr Thr Tyr Thr Asp Ile
            1460                 1465                 1470

Ser Thr Gly Phe Phe Glu Gln Ala Arg Glu Gln Phe Ala Pro Phe Glu
    1475                 1480                 1485

Asp Arg Met Val Phe Glu Pro Leu Asp Ile Arg Arg Ser Pro Ala Glu
    1490                 1495                 1500

Gln Gly Phe Glu Pro His Ala Tyr Asp Leu Ile Ile Ala Ser Asn Val
1505                 1510                 1515                 1520

Leu His Ala Thr Pro Asp Leu Glu Lys Thr Met Ala His Ala Arg Ser
                1525                 1530                 1535

Leu Leu Lys Pro Gly Gly Gln Met Val Ile Leu Glu Ile Thr His Lys
            1540                 1545                 1550

Glu His Thr Arg Leu Gly Phe Ile Phe Gly Leu Phe Ala Asp Trp Trp
    1555                 1560                 1565

Ala Gly Val Asp Asp Gly Arg Cys Thr Glu Pro Phe Val Ser Phe Asp
1570                 1575                 1580

Arg Trp Asp Ala Ile Leu Lys Arg Val Gly Phe Ser Gly Val Asp Ser
1585                 1590                 1595                 1600

Arg Thr Thr Asp Arg Asp Ala Asn Leu Phe Pro Thr Ser Val Phe Ser
                1605                 1610                 1615

Thr His Ala Ile Asp Ala Thr Val Glu Tyr Leu Asp Ala Pro Leu Ala
            1620                 1625                 1630

Ser Ser Gly Thr Val Lys Asp Ser Tyr Pro Pro Leu Val Val Val Gly
    1635                 1640                 1645

Gly Gln Thr Pro Gln Ser Gln Arg Leu Leu Asn Asp Ile Lys Ala Ile
    1650                 1655                 1660

Met Pro Pro Arg Pro Leu Gln Thr Tyr Lys Arg Leu Val Asp Leu Leu
1665                 1670                 1675                 1680

Asp Ala Glu Glu Leu Pro Met Lys Ser Thr Phe Val Met Leu Thr Glu
                1685                 1690                 1695

Leu Asp Glu Glu Leu Phe Ala Gly Leu Thr Glu Glu Thr Phe Glu Ala
            1700                 1705                 1710

Thr Lys Leu Leu Leu Thr Tyr Ala Ser Asn Thr Val Trp Leu Thr Glu
    1715                 1720                 1725

Asn Ala Trp Val Gln His Pro His Gln Ala Ser Thr Ile Gly Met Leu

-continued

```
                 1730                      1735                      1740
Arg  Ser  Ile  Arg  Arg  Glu  His  Pro  Asp  Leu  Gly  Val  His  Val  Leu  Asp
1745                1750                     1755                          1760

Val  Asp  Ala  Val  Glu  Thr  Phe  Asp  Ala  Thr  Phe  Leu  Val  Glu  Gln  Val
                    1765                     1770                     1775

Leu  Arg  Leu  Glu  Glu  His  Thr  Asp  Glu  Leu  Ala  Ser  Ser  Thr  Thr  Trp
                    1780                     1785                     1790

Thr  Gln  Glu  Pro  Glu  Val  Ser  Trp  Cys  Lys  Gly  Arg  Pro  Trp  Ile  Pro
                    1795                     1800                     1805

Arg  Leu  Lys  Arg  Asp  Leu  Ala  Arg  Asn  Asn  Arg  Met  Asn  Ser  Ser  Arg
     1810                     1815                     1820

Arg  Pro  Ile  Tyr  Glu  Met  Ile  Asp  Ser  Ser  Arg  Ala  Pro  Val  Ala  Leu
1825                1830                     1835                          1840

Gln  Thr  Ala  Arg  Asp  Ser  Ser  Ser  Tyr  Phe  Leu  Glu  Ser  Ala  Glu  Thr
                    1845                     1850                     1855

Trp  Phe  Val  Pro  Glu  Ser  Val  Gln  Gln  Met  Glu  Thr  Lys  Thr  Ile  Tyr
                    1860                     1865                     1870

Val  His  Phe  Ser  Cys  Pro  His  Ala  Leu  Arg  Val  Gly  Gln  Leu  Gly  Phe
          1875                     1880                     1885

Phe  Tyr  Leu  Val  Gln  Gly  His  Val  Gln  Glu  Gly  Asn  Arg  Glu  Val  Pro
     1890                     1895                     1900

Val  Val  Ala  Leu  Ala  Glu  Arg  Asn  Ala  Ser  Ile  Val  His  Val  Arg  Pro
1905                     1910                     1915                     1920

Asp  Tyr  Ile  Tyr  Thr  Glu  Ala  Asp  Asn  Asn  Leu  Ser  Glu  Gly  Gly  Gly
                    1925                     1930                     1935

Ser  Leu  Met  Val  Thr  Val  Leu  Ala  Ala  Ala  Val  Leu  Ala  Glu  Thr  Val
               1940                     1945                     1950

Ile  Ser  Thr  Ala  Lys  Cys  Leu  Gly  Val  Thr  Asp  Ser  Ile  Leu  Val  Leu
               1955                     1960                     1965

Asn  Pro  Pro  Ser  Ile  Cys  Gly  Gln  Met  Leu  Leu  His  Ala  Gly  Glu  Glu
               1970                     1975                     1980

Ile  Gly  Leu  Gln  Val  His  Leu  Ala  Thr  Thr  Ser  Gly  Asn  Arg  Ser  Ser
1985                     1990                     1995                     2000

Val  Ser  Ala  Gly  Asp  Ala  Lys  Ser  Trp  Leu  Thr  Leu  His  Ala  Arg  Asp
                    2005                     2010                     2015

Thr  Asp  Trp  His  Leu  Arg  Arg  Val  Leu  Pro  Arg  Gly  Val  Gln  Ala  Leu
                    2020                     2025                     2030

Val  Asp  Leu  Ser  Ala  Asp  Gln  Ser  Cys  Glu  Gly  Leu  Thr  Gln  Arg  Met
                    2035                     2040                     2045

Met  Lys  Val  Leu  Met  Pro  Gly  Cys  Ala  His  Tyr  Arg  Ala  Ala  Asp  Leu
     2050                     2055                     2060

Phe  Thr  Asp  Thr  Val  Ser  Thr  Glu  Leu  His  Ser  Gly  Ser  Arg  His  Gln
2065                2070                     2075                          2080

Ala  Ser  Leu  Pro  Ala  Ala  Tyr  Trp  Glu  His  Val  Val  Ser  Leu  Ala  Arg
                    2085                     2090                     2095

Gln  Gly  Leu  Pro  Ser  Val  Ser  Glu  Gly  Trp  Glu  Val  Met  Pro  Cys  Thr
                    2100                     2105                     2110

Gln  Phe  Ala  Ala  His  Ala  Asp  Lys  Thr  Arg  Pro  Asp  Leu  Ser  Thr  Val
          2115                     2120                     2125

Ile  Ser  Trp  Pro  Arg  Glu  Ser  Asp  Glu  Ala  Thr  Leu  Pro  Thr  Arg  Val
     2130                     2135                     2140

Arg  Ser  Ile  Asp  Ala  Glu  Thr  Leu  Phe  Ala  Ala  Asp  Lys  Thr  Tyr  Leu
     2145                     2150                     2155                2160
```

-continued

Leu Val Gly Leu Thr Gly Asp Leu Gly Arg Ser Leu Gly Arg Trp Met
                2165                    2170                2175
Val Gln His Gly Ala Cys His Ile Val Leu Thr Ser Arg Asn Pro Gln
                2180                    2185                2190
Val Asn Pro Lys Trp Leu Ala His Val Glu Glu Leu Gly Gly Arg Val
                2195                    2200                2205
Thr Val Leu Ser Met Asp Val Thr Ser Gln Asn Ser Val Glu Ala Gly
                2210                    2215                2220
Leu Ala Lys Leu Lys Asp Leu His Leu Pro Pro Val Gly Gly Ile Ala
2225                 2230                    2235                2240
Phe Gly Pro Leu Val Leu Gln Asp Val Met Leu Asn Asn Met Glu Leu
                2245                    2250                2255
Pro Met Met Glu Met Val Leu Asn Pro Lys Val Glu Gly Val Arg Ile
                2260                    2265                2270
Leu His Glu Lys Phe Ser Asp Pro Thr Ser Ser Asn Pro Leu Asp Phe
                2275                    2280                2285
Phe Val Met Phe Ser Ser Ile Val Ala Val Met Gly Asn Pro Gly Gln
                2290                    2295                2300
Ala Asn Tyr Ser Ala Ala Asn Cys Tyr Leu Gln Ala Leu Ala Gln Gln
2305                 2310                    2315                2320
Arg Val Ala Ser Gly Leu Ala Ala Ser Thr Ile Asp Ile Gly Ala Val
                2325                    2330                2335
Tyr Gly Val Gly Phe Val Thr Arg Ala Glu Leu Glu Glu Asp Phe Asn
                2340                    2345                2350
Ala Ile Arg Phe Met Phe Asp Ser Val Glu Glu His Glu Leu His Thr
                2355                    2360                2365
Leu Phe Ala Glu Ala Val Val Ala Gly Arg Arg Ala Val His Gln Gln
                2370                    2375                2380
Glu Gln Gln Arg Lys Phe Ala Thr Val Leu Asp Met Ala Asp Leu Glu
2385                 2390                    2395                2400
Leu Thr Thr Gly Ile Pro Pro Leu Asp Pro Ala Leu Lys Asp Arg Ile
                2405                    2410                2415
Thr Phe Phe Asp Asp Pro Arg Ile Gly Asn Leu Lys Ile Pro Glu Tyr
                2420                    2425                2430
Arg Gly Ala Lys Ala Gly Glu Gly Ala Ala Gly Ser Lys Gly Ser Val
                2435                    2440                2445
Lys Glu Gln Leu Leu Gln Ala Thr Asn Leu Asp Gln Val Arg Gln Ile
                2450                    2455                2460
Val Ile Asp Gly Leu Ser Ala Lys Leu Gln Val Thr Leu Gln Ile Pro
2465                 2470                    2475                2480
Asp Gly Glu Ser Val His Pro Thr Ile Pro Leu Ile Asp Gln Gly Val
                2485                    2490                2495
Asp Ser Leu Gly Ala Val Thr Val Gly Thr Trp Phe Ser Lys Gln Leu
                2500                    2505                2510
Tyr Leu Asp Leu Pro Leu Leu Lys Val Leu Gly Gly Ala Ser Ile Thr
                2515                    2520                2525
Asp Leu Ala Asn Glu Ala Ala Ala Arg Leu Pro Pro Ser Ser Ile Pro
                2530                    2535                2540
Leu Val Ala Ala Thr Asp Gly Gly Ala Glu Ser Thr Asp Asn Thr Ser
2545                 2550                    2555                2560
Glu Asn Glu Val Ser Gly Arg Glu Asp Thr Asp Leu Ser Ala Ala Ala
                2565                    2570                2575
Thr Ile Thr Glu Pro Ser Ser Ala Asp Glu Asp Thr Glu Pro Gly
                2580                    2585                2590

```
Asp Glu Asp Val Pro Arg Ser His His Pro Leu Ser Leu Gly Gln Glu
        2595                2600                2605

Tyr Ser Trp Arg Ile Gln Gln Gly Ala Glu Asp Pro Thr Val Phe Asn
        2610                2615                2620

Asn Thr Ile Gly Met Phe Met Lys Gly Ser Ile Asp Leu Lys Arg Leu
2625                2630                2635                2640

Tyr Lys Ala Leu Arg Ala Val Leu Arg Arg His Glu Ile Phe Arg Thr
                2645                2650                2655

Gly Phe Ala Asn Val Asp Glu Asn Gly Met Ala Gln Leu Val Phe Gly
            2660                2665                2670

Gln Thr Lys Asn Lys Val Gln Thr Ile Gln Val Ser Asp Arg Ala Gly
            2675                2680                2685

Ala Glu Glu Gly Tyr Arg Gln Leu Val Gln Thr Arg Tyr Asn Pro Ala
        2690                2695                2700

Ala Gly Asp Thr Leu Arg Leu Val Asp Phe Phe Trp Gly Gln Asp Asp
2705                2710                2715                2720

His Leu Leu Val Val Ala Tyr His Arg Leu Val Gly Asp Gly Ser Thr
                2725                2730                2735

Thr Glu Asn Ile Phe Val Glu Ala Gly Gln Leu Tyr Asp Gly Thr Ser
            2740                2745                2750

Leu Ser Pro His Val Pro Gln Phe Ala Asp Leu Ala Ala Arg Gln Arg
            2755                2760                2765

Ala Met Leu Glu Asp Gly Arg Met Glu Glu Asp Leu Ala Tyr Trp Lys
        2770                2775                2780

Lys Met His Tyr Arg Pro Ser Ser Ile Pro Val Leu Pro Leu Met Arg
2785                2790                2795                2800

Pro Leu Val Gly Asn Ser Ser Arg Ser Asp Thr Pro Asn Phe Gln His
            2805                2810                2815

Cys Gly Pro Trp Gln Gln His Glu Ala Val Ala Arg Leu Asp Pro Met
        2820                2825                2830

Val Ala Phe Arg Ile Lys Glu Arg Ser Arg Lys His Lys Ala Thr Pro
        2835                2840                2845

Met Gln Phe Tyr Leu Ala Ala Tyr Gln Val Leu Leu Ala Arg Leu Thr
        2850                2855                2860

Asp Ser Thr Asp Leu Thr Val Gly Leu Ala Asp Thr Asn Arg Ala Thr
2865                2870                2875                2880

Val Asp Glu Met Ala Ala Met Gly Phe Phe Ala Asn Leu Leu Pro Leu
            2885                2890                2895

Arg Phe Arg Asp Phe Arg Pro His Ile Thr Phe Gly Glu His Leu Ile
        2900                2905                2910

Ala Thr Arg Asp Leu Val Arg Glu Ala Leu Gln His Ala Arg Val Pro
        2915                2920                2925

Tyr Gly Val Leu Leu Asp Gln Leu Gly Leu Glu Val Pro Val Pro Thr
        2930                2935                2940

Ser Asn Gln Pro Ala Pro Leu Phe Gln Ala Val Phe Asp Tyr Lys Gln
2945                2950                2955                2960

Gly Gln Ala Glu Ser Gly Thr Ile Gly Gly Ala Lys Ile Thr Glu Val
            2965                2970                2975

Ile Ala Thr Arg Glu Arg Thr Pro Tyr Asp Val Val Leu Glu Met Ser
            2980                2985                2990

Asp Asp Pro Thr Lys Asp Pro Leu Leu Thr Ala Lys Leu Gln Ser Ser
        2995                3000                3005

Arg Tyr Glu Ala His His Pro Gln Ala Phe Leu Glu Ser Tyr Met Ser
```

|  | 3010 |  |  |  | 3015 |  |  |  | 3020 |  |  |
|---|---|---|---|---|---|---|---|---|---|---|---|
| Leu | Leu | Ser | Met | Phe | Ser | Met | Asn | Pro | Ala | Leu | Lys | Leu | Ala |
| 3025 |  |  |  |  | 3030 |  |  |  | 3035 |  |  |

( 2 ) INFORMATION FOR SEQ ID NO:3:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: probe ( x i ) SEQUENCE DESCRIPTION: SEQ ID NO:3:

GATACGGCAT GCAGCTCGTC GTTGGTTGCC GTTCATCTGG CTGCA   45